(12) United States Patent
Hyde et al.

(10) Patent No.: US 9,433,692 B2
(45) Date of Patent: Sep. 6, 2016

(54) NON-THERMAL ELECTROMAGNETIC STERILIZATION

(71) Applicant: Elwha LLC, Bellevue, WA (US)

(72) Inventors: Roderick A. Hyde, Redmond, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 215 days.

(21) Appl. No.: 14/064,507

(22) Filed: Oct. 28, 2013

(65) Prior Publication Data
US 2015/0118106 A1    Apr. 30, 2015

(51) Int. Cl.
*A61L 2/00* (2006.01)
*A61L 2/08* (2006.01)

(52) U.S. Cl.
CPC .............. *A61L 2/08* (2013.01); *A61L 2202/14* (2013.01)

(58) Field of Classification Search
CPC ............................. A61L 2/08; A61L 2202/14
USPC ................................................... 422/22, 290
See application file for complete search history.

(56) References Cited

U.S. PATENT DOCUMENTS

| | | | |
|---|---|---|---|
| 4,599,216 A | 7/1986 | Rohrer et al. | |
| 4,839,485 A | 6/1989 | Koch et al. | |
| 5,962,054 A | 10/1999 | Kozempel et al. | |
| 7,520,667 B2 | 4/2009 | Pahlsson et al. | |
| 7,570,409 B1 * | 8/2009 | Wang ......................... | G02F 1/31 257/17 |
| 2005/0069089 A1 * | 3/2005 | Armstrong .............. | A61B 6/025 378/162 |
| 2005/0127068 A1 * | 6/2005 | Tang ...................... | H05B 6/701 219/700 |
| 2007/0265523 A1 | 11/2007 | Pahlsson et al. | |
| 2009/0092708 A1 | 4/2009 | Alvarado et al. | |
| 2009/0283517 A1 * | 11/2009 | Mackay ................. | H05B 6/782 219/700 |
| 2010/0115785 A1 | 5/2010 | Ben-Shmuel et al. | |
| 2011/0117202 A1 * | 5/2011 | Bourke, Jr. ........ | H05B 41/2806 424/490 |
| 2012/0164022 A1 | 6/2012 | Muginstein et al. | |

* cited by examiner

*Primary Examiner* — Kevin Joyner

(57) ABSTRACT

The present disclosure provides systems and methods associated with non-thermal electroporation. One or more electromagnetic radiation sources may be used to generate an interference pattern having at least one antinode. The electric field associated with the antinode may be configured to cause irreversible electroporation. Thus, the antinode may be suitable for at least partial sterilization by rendering cells as non-viable through electroporation. An antinode may be formed by constructive interference of two or more lobes of two or more radiation sources. An antinode may be spatially varied with respect to an object, volume, and/or surface. A controller may spatially vary an antinode according to an electroporation pattern, such as a stochastic or rasterizing pattern, to achieve a desired sterilization level and/or maintain a temperature characteristic (e.g., absolute temperature, relative temperature, and/or rate of change) with a threshold range.

19 Claims, 18 Drawing Sheets

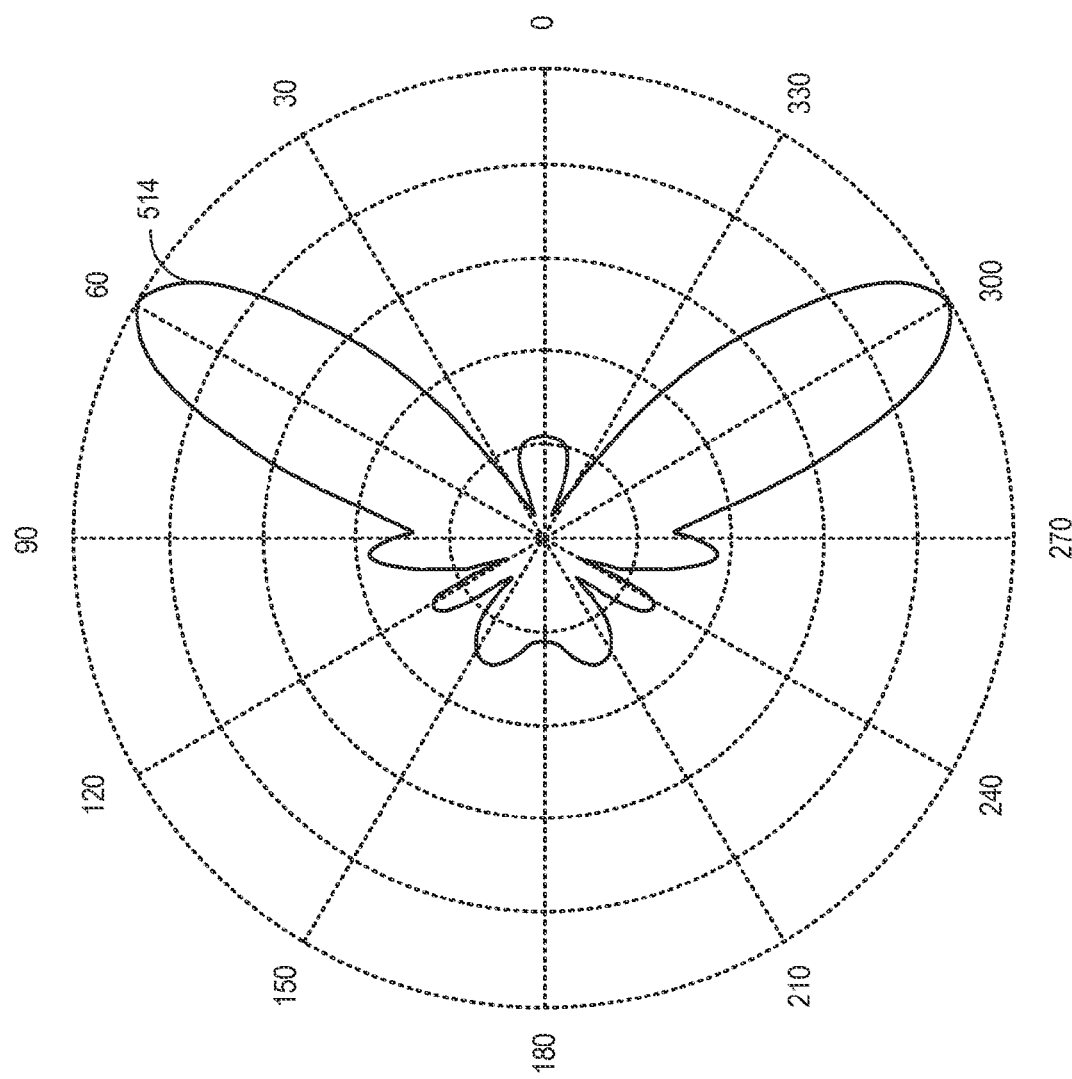

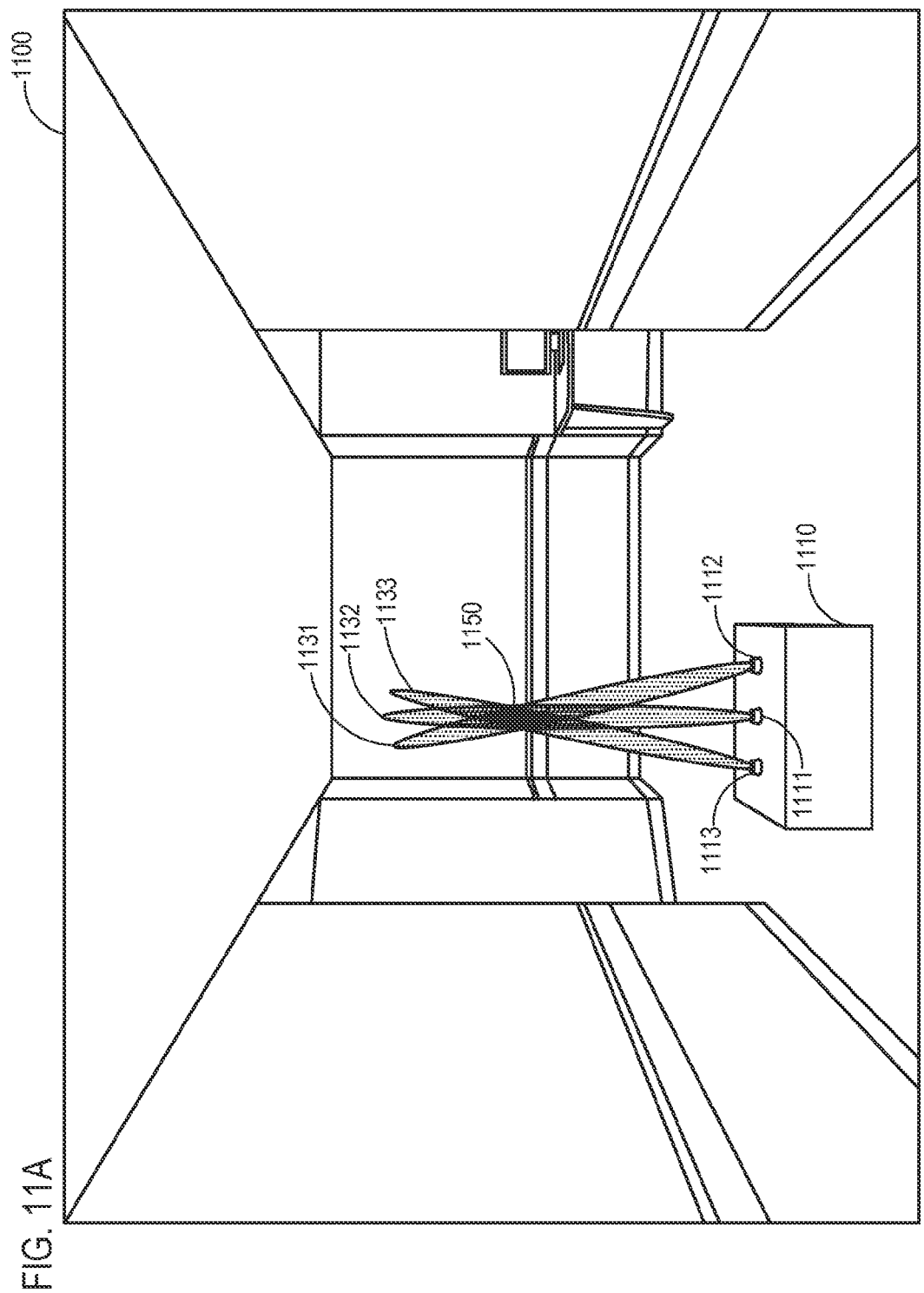

NON-THERMAL ELECTROMAGNETIC STERILIZATION

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 U.S.C. §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

NONE

RELATED APPLICATIONS

U.S. patent application Ser. No. 14/064,504, titled "Non-Thermal Electromagnetic Sterilization," naming Roderick A. Hyde and Lowell L. Wood, Jr. as inventors, filed Oct. 28, 2013 with is related to the present application.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

TECHNICAL FIELD

This disclosure relates to sterilization using electromagnetic radiation. Specifically, this disclosure relates to non-thermal sterilization by electroporation.

SUMMARY

The present disclosure includes various systems and methods for non-thermal electroporation. For example, in one embodiment, one or more electromagnetic radiation generators are used to generate electromagnetic radiation with an interference pattern having at least one antinode. A single electromagnetic radiation generator may be used to create multiple electromagnetic sources, such as via apertures, slits, or other openings in a panel. An attribute of an electric field associated with the at least one antinode is configured to cause electroporation.

The electroporating antinode may be formed by the constructive interference of two or more lobes of two or more radiation sources, where the electromagnetic radiation sources are created using one or more electromagnetic radiation generators.

According to various embodiments, a controller may spatially vary a location of the at least one antinode with respect to an object with a region. That is, the controller may move the antinode, cause the antinode to be moved, move the object, and/or cause the object to be moved. The relative movement of the at least one antinode may correspond to an electroporation pattern configured to regulate the generation of heat within the object and/or to ensure that at least a portion of the object is subjected to sufficiently high-peak-electric fields to cause sterilizing electroporation.

The electroporation may be irreversible electroporation, such that the cells become non-viable. Accordingly, the electroporation pattern may be configured to at least partially sterilize a portion of the object using the at least one antinode while regulating the generation of heat within the object or portion of the object.

In various embodiments, the regulation of the generation of heat may include maintaining the temperature below a threshold value. The regulation of the generation of heat may also relate to maintaining a rate of temperature increase below a threshold value. The regulation of the generation of heat may also relate to maintaining a temperature within a predetermined temperature range.

In some embodiments, an electroporation system may be configured to electroporate the surfaces of and/or objects within a room. Additionally, the electroporation system may be configured to electroporate the air or other fluid within the volume. An electroporation pattern may be utilized to achieve a desired sterilization and/or a desired temperature increase or rate of temperature increase. The temperature may be associated with the entire volume and/or a region of the volume. The temperature thresholds may vary based on the detected object or portion of the volume. For example, a maximum temperature threshold for air within a volume may be different than the maximum temperature threshold for a surface of an object within the volume.

BRIEF DESCRIPTION OF THE DRAWINGS

FIG. 5E illustrates a multi-source field strength pattern according to another embodiment.

FIG. 11A illustrates a non-thermal electroporation system configured to sterilize a room.

DETAILED DESCRIPTION

Figure 1:
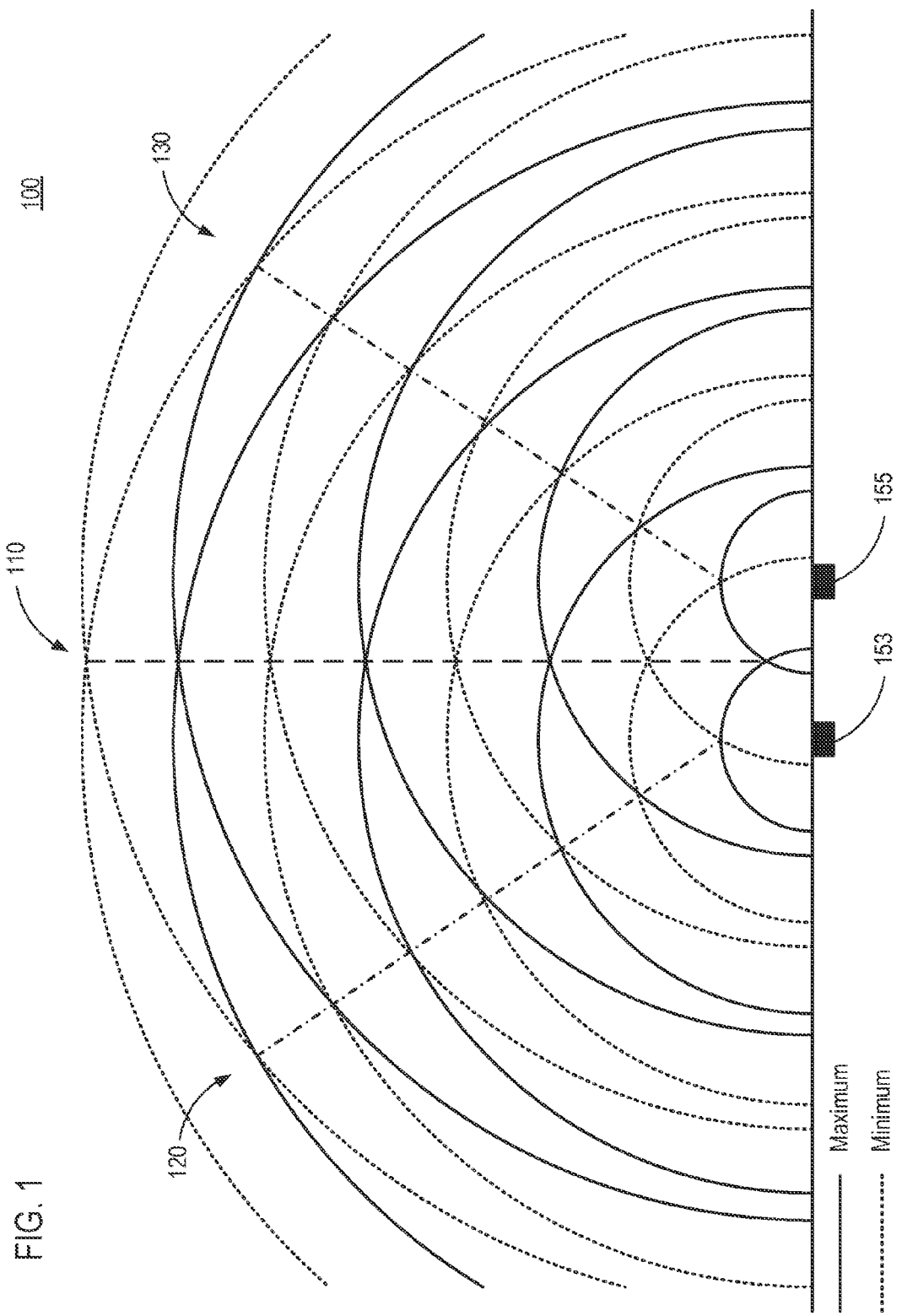
FIG. 1 illustrates overlapping electromagnetic radiation from two electromagnetic radiation sources.

According to the various embodiments described herein, electromagnetic radiation is used to at least partially sterilize an object or volume. Electromagnetic radiation having characteristics suitable for electroporation may be directed to a specific volume. The electroporation of the volume may, at least partially, sterilize the volume.

According to various embodiments, the electromagnetic radiation may non-thermally electroporate a volume. In various embodiments, an interference pattern of one or more electromagnetic fields may be used to generate a high-peak-field to electroporate a volume. In some embodiments, constructive interference within an electromagnetic interference pattern may generate at least one antinode suitable to electroporate an object or volume (the terms object and volume are used interchangeably in many instances herein).

In various embodiments, the electroporating antinode and the volume to be electroporated may be spatially varied (moved) with respect to one another. In various embodiments, a spatial variation device may spatially vary the electroporating antinode with respect to the volume to be electroporated. The spatial variation device may be configured to vary the amplitude and/or the phase of the generated electromagnetic radiation, utilize one or more diffractive, refractive and/or reflective elements, move the volume with respect to the radiation sources, and/or move the radiation sources with respect to the volume.

In some embodiments, the electroporating antinode may be moved by moving one or more of the radiation generators and/or one or more slits/apertures functioning as radiation sources. The electroporating antinode may also be moved by varying a phase of one or more of the radiation generators and/or the slits/apertures functioning as radiation sources. Alternatively or additionally, the volume may be moved with respect to the electroporating antinode. In some embodiments, a controller may vary the amplitude and/or the frequency of the electromagnetic radiation from one or more of the electromagnetic radiation generators and/or electromagnetic radiation sources. Although the electroporating antinode is described as electroporating a volume, it is appreciated that a surface may be electroporated instead of or in addition to a volume.

The controller may spatially vary a location of the antinode using a phase shifter, using a variable resonance, using a tunable reactance, by moving the volume to be electroporated, by varying the emission from a radiation source, by moving a radiation source, by moving a radiation generator, using a mechanically steerable transmitter, using a beam-director to deflect electromagnetic radiation, using a lens to focus the electromagnetic radiation, and/or any combination thereof. In some embodiments, metamaterial elements can be used to control electromagnetic patterns (e.g., for beam-directors, lenses, resonant structures, etc.).

According to various embodiments, one or more electromagnetic radiation sources may be used to generate an interference pattern with one or more antinodes. In some embodiments, a single electromagnetic radiation generator may be used in combination with one or more slits, diffractive elements, reflective elements, refractive elements, apertures, and/or the like to generate at least one electroporating antinode within an interference pattern. In various embodiments, a single electromagnetic radiation generator may supply each electromagnetic radiation source (e.g., a point source or an approximate point source) with electromagnetic radiation. In other embodiments, multiple electromagnetic radiation generators may supply electromagnetic radiation to multiple electromagnetic radiation sources. Accordingly, the number of electromagnetic radiation generators and the number of electromagnetic radiation sources may be a 1:1 mapping, a 1:N mapping, or an N:M mapping, where N and M are integers greater than 0.

In various embodiments, an electroporating system may include one or more electromagnetic radiation generators and/or radiation sources, a spatial variation device, and a controller to control the relative spatial variation of the at least one antinode according to an electroporation pattern. The electroporation pattern may be configured to regulate the generation of heat within the volume and/or to ensure that a predetermined level of sterilization occurs.

The electromagnetic radiation generators and/or source may include one or more electronically steerable antenna arrays, one or more transmitters, one or more antennas, and/or other director, beam former, point source creator, or the like. For example, one or more of the radiation sources may comprise a metamaterial surface antenna (e.g., using microwave surface antenna technology from Kymeta Corporation). The electromagnetic radiation may be generated by discrete generators or by a single generator. In some embodiments, magnetrons may be used to generate electromagnetic radiation. For instance, a magnetron of, or similar to that of, a consumer microwave oven may be used to generate electromagnetic radiation for use in any of the various systems and methods described herein.

In various embodiments, a controller and/or sensor may monitor one or more temperatures associated with the volume or object. A controller may modify the amplitude, location of the electroporating electromagnetic radiation, and/or a pattern for electroporating a volume to regulate the generation of heat. In some embodiments, it may be desirable to maintain the temperature of a volume below a specific threshold and/or maintain a rate of temperature increase (or decrease) below (or above) a threshold.

For instance, the threshold temperature (or time at/above the threshold temperature) may be selected to avoid protein deformation or denaturation. In some embodiments, the temperature sensor may be used to determine the temperature at a specific location within the object, temperatures at a plurality of locations within the object, a peak temperature within the object, and/or a surface temperature of the object. The sensor used to measure temperature may include thermometers inserted within the object, thermometers contacting the surface of the object, or non-contact thermometers. Non-contact thermometers may include infrared photodetectors or cameras to detect infrared radiation emitted from the surface of the object (e.g., forming a thermogram), or may include microwave radiometers to detect microwave radiation emitted from the interior of the object.

In some embodiments, the electromagnetic radiation may be generated in pulses and a controller may adjust the power, frequency, pulse length, pulse spacing, pulse duty factor, and/or pulse shape in response to a measured temperature associated with a volume. A controller or other component in communication with the controller may vary one or more attributes of the electromagnetic radiation, whether it is a pulse, DC transmission, and/or AC transmission, such as a pulse length, a pulse spacing, a pulse duty factor, a pulse shape, and/or other characteristic.

In some embodiments, the electroporation pattern may be modified to include a cooling period and/or to avoid adjacent locations on the object to maintain a temperature of the object below a heating threshold. In some embodiments, a controller may implement a stochastic electroporation pattern, such that the antinode is moved (relatively speaking) to random locations while still electroporating the entire volume. In some embodiments, the controller may implement a rasterized electroporation pattern, such that the antinode sequentially overlaps various regions of the volume. In some embodiments, the object may be actively cooled. For example, the object may be actively cooled when a detected or measured temperature exceeds a threshold value. Cooling can involve a variety of techniques, including lowering an ambient temperature of the object's environment, lowering a temperature of a surface contacting the object, applying a cooling fluid to the object, directing cool air/gas to the object, contacting the object with a vaporizable fluid, or the like.

The controller may implement a multi-pass electroporation pattern, such that the antinode passes over at least some locations more than one time. One or more attributes of the antinode may be varied between successive passes. In some embodiments, electroporation may be paused during a rest period between successive passes. In some embodiments, the controller may implement a Moiré pattern having one or more antinodes for electroporating the volume. A controller may automatically determine an appropriate electroporation pattern and/or allow a user to select from a variety of electroporation patterns.

In some embodiments, the electroporating antinode(s) may be caused by the constructive interference of one or more intersecting beam-formed electromagnetic radiation patterns. The antinode may electroporate the object to achieve a specific amount of sterilization. The specific amount of sterilization may be measured by an intensity of the electric field and/or a time of exposure to the electric field. The time of exposure may correspond to the intensity of the electric field. The specific amount of sterilization may correspond to a composition of the object where different compositions are sterilized to different degrees.

The specific amount of sterilization may also correspond to a known type of bacteria or other sterilizable entity. In various embodiments, each electroporated region of a volume to be electroporated may be subjected to a minimum intensity of an electric field for a particular amount of time.

The amount of time may vary inversely with the intensity of the electric field. The time and/or intensity for electroporation may be determined using one or more sensors and may be associated with a type of volume/object being electroporated, the type of cell desired to kill, the color of the object, the mass of the object, the shape of the object, and/or other characteristic of the object being sterilized.

For example, for a portion of meat comprising both fat and flesh, the fat may be sterilized to a different degree than the flesh. As another example, for a piece of fruit comprising stem and flesh, the stem may be sterilized to a different degree than the flesh. Similarly, for a portion of meat, portions of the meat to a first depth (e.g., a surface depth less than a centimeter) may be sterilized to a different degree than portions of the meat deeper than the first depth (e.g., deeper than a centimeter).

In certain embodiments, the controller may generate or utilize a pre-generated three-dimensional or two-dimensional electroporation pattern. In some embodiments, the electroporating antinode may have a sufficient volume for some objects that a one-dimensional electroporation pattern may be utilized. That is, the portion of the antinode capable of electroporating may not be a single point, rather it may have a volume with a depth, width, and length. If the width, depth, and/or length of the electroporating antinode sufficiently encompasses one or more dimensions of a volume to be electroporated, then a one- or two-dimensional electroporation pattern may be sufficient to electroporate the entirety of the volume.

In various embodiments, the electroporation pattern may be based on a two- or three-dimensional model of the volume to be electroporated (also referred to as the object). The three-dimensional model may correspond to the shape of the object. One or more sensors may automatically determine the shape of the volume to be electroporated, or a user may manually enter the shape. The electroporation pattern may cause the antinode to deliver more energy to different portions of the three-dimensional model.

For example, the antinode may deliver more energy to the surface of the model than to the interior of the model. The model may be determined using one or more sensors and/or based on one or more images, including sonic images, visible light images, and/or non-visible light images (e.g., infrared, x-ray, etc.). A laser may be utilized to determine a characteristic of the volume to be electroporated, including the shape of the volume. Other sensor types, such as triangulation scanner, stereoscopic cameras, and/or other sensor may be utilized.

In various embodiments, the electroporation pattern (e.g., stochastic, rasterized, Moiré, etc.) may be determined with respect to a two-dimensional projection of the object. Such a pattern based on a two-dimensional projection may be executed in layers to electroporate the entire three-dimensional volume. To regulate the increase in temperature during electroporation, a stochastic pattern may include a sequence of random or pseudo-random locations to minimize spatially adjacent locations from being electroporated too close in time.

The various systems and methods described herein may utilize any of a wide variety of electroporation techniques and technologies. For a given pulse duration and shape, a transmembrane voltage threshold may exist for cells. The transmembrane voltage threshold voltage may be different depending on the type of cell or cells and/or based on a desired reliability. Electroporation, as used herein, may refer to a transmembrane voltage sufficient to compromise the viability of the cells resulting in irreversible electroporation.

The electromagnetic radiation may be transmitted as pulses, at a relatively low radiation frequency and/or at a relatively high radiation frequency. Some radiation frequencies may be more efficient than others given the frequency dependence of irreversible electroporation, especially at lower frequencies. However, any of a wide variety of frequency ranges may be utilized, including 2.4 GHz electromagnetic radiation from consumer magnetrons. Other frequencies between approximately 1 KHz and 300 GHz, or even terahertz frequencies may also be utilized. Additionally, pulse width modulation may be utilized with any suitable pulse duty cycle.

In some embodiments, the electromagnetic radiation may have a center frequency in the ISM (Industrial, Scientific, Medical) band. In other embodiments, the electromagnetic radiation may be infrared radiation. The electromagnetic radiation may be configured to kill or inhibit growth of microbes (including bacteria, algae, and fungi) via electroporation.

Characteristics of the electroporating electromagnetic radiation may be chosen to effect a particular strain of bacteria, fungus, microbe, or other cellular entity. Accordingly, the electromagnetic radiation may be at one or more useful frequencies, including frequencies between 1 GHz and 300 GHz, 2.45 GHz, 4.5 GHz 9.5 GHz, 42.2 GHz, a frequency in the ISM band, 915 MHz, and/or a frequency between 300 GHz and 1 THz.

Many existing computing devices and infrastructures may be used in combination with the presently described systems and methods. Some of the infrastructure that can be used with embodiments disclosed herein is already available, such as general-purpose computers, computer programming tools and techniques, digital storage media, and communication links. A computing device or controller may include a processor such as a microprocessor, a microcontroller, logic circuitry, or the like. A processor may include a special purpose processing device such as application-specific integrated circuits (ASIC), programmable array logic (PAL), programmable logic array (PLA), programmable logic device (PLD), field programmable gate array (FPGA), or other customizable and/or programmable device. The computing device may also include a machine-readable storage device such as non-volatile memory, static RAM, dynamic RAM, ROM, CD-ROM, disk, tape, magnetic, optical, flash memory, or other machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

FIG. 1 illustrates overlapping electromagnetic radiation 100 from two electromagnetic radiation sources 153 and 155. In the illustrated embodiment, solid lines concentric with electromagnetic radiation source 153 represent maximums of the electromagnetic radiation of the electromagnetic radiation source 153. Dashed lines concentric with the electromagnetic radiation source 153 represent minimums of the electromagnetic radiation of the electromagnetic radiation source 153. Similarly, solid lines and dashed lines concentric with the electromagnetic radiation source 155 represent maximums and minimums, respectively, of the electromagnetic radiation source 155.

Each electromagnetic radiation source 153 and 155 may be a distinct electromagnetic radiation generator. Alternatively, each radiation source 153 and 155 may be created from (i.e., utilize electromagnetic radiation generated by) the same electromagnetic radiation generator using apertures, slits, cross slits, lenses, mirrors, antennas, repeaters, and/or other device(s) for manipulating electromagnetic radiation.

As will be appreciated, constructive interference of the electromagnetic radiation from the two electromagnetic radiation sources 153 and 155 at and near center line 110 may increase the electric field in the surrounding region. Likewise, destructive interference of the electromagnetic radiation at and near lines 120 and 130 may decrease the electric field in the surrounding regions.

According to various embodiments, any number of radiation sources may be utilized in conjunction with one another to attain a directed or more focused region of high-electric field. The center line 110 may include an antinode at each point of maximum (or minimum) constructive interference. In some embodiments, the electric field at each antinode may be sufficiently strong to cause electroporation. In other embodiments, the antinode may be specifically adapted to not be sufficiently strong to cause electroporation. In such embodiments, the overlap of additional beam-formed electromagnetic radiation may be required to attain electric fields sufficiently strong to cause electroporation.

Additional electromagnetic radiation sources (created by the same or different electromagnetic radiation generators) may be arranged in any of a wide variety of configurations relative to one another, including coplanar and non-coplanar configurations in three-dimensional space, to attain a desired beam-formed electromagnetic radiation pattern. In some embodiments, the electromagnetic radiation pattern comprises traveling electromagnetic waves. In some embodiments (e.g., where at least some of the volume is located within a cavity), the electromagnetic radiation pattern comprises standing electromagnetic waves.

Figure 2:
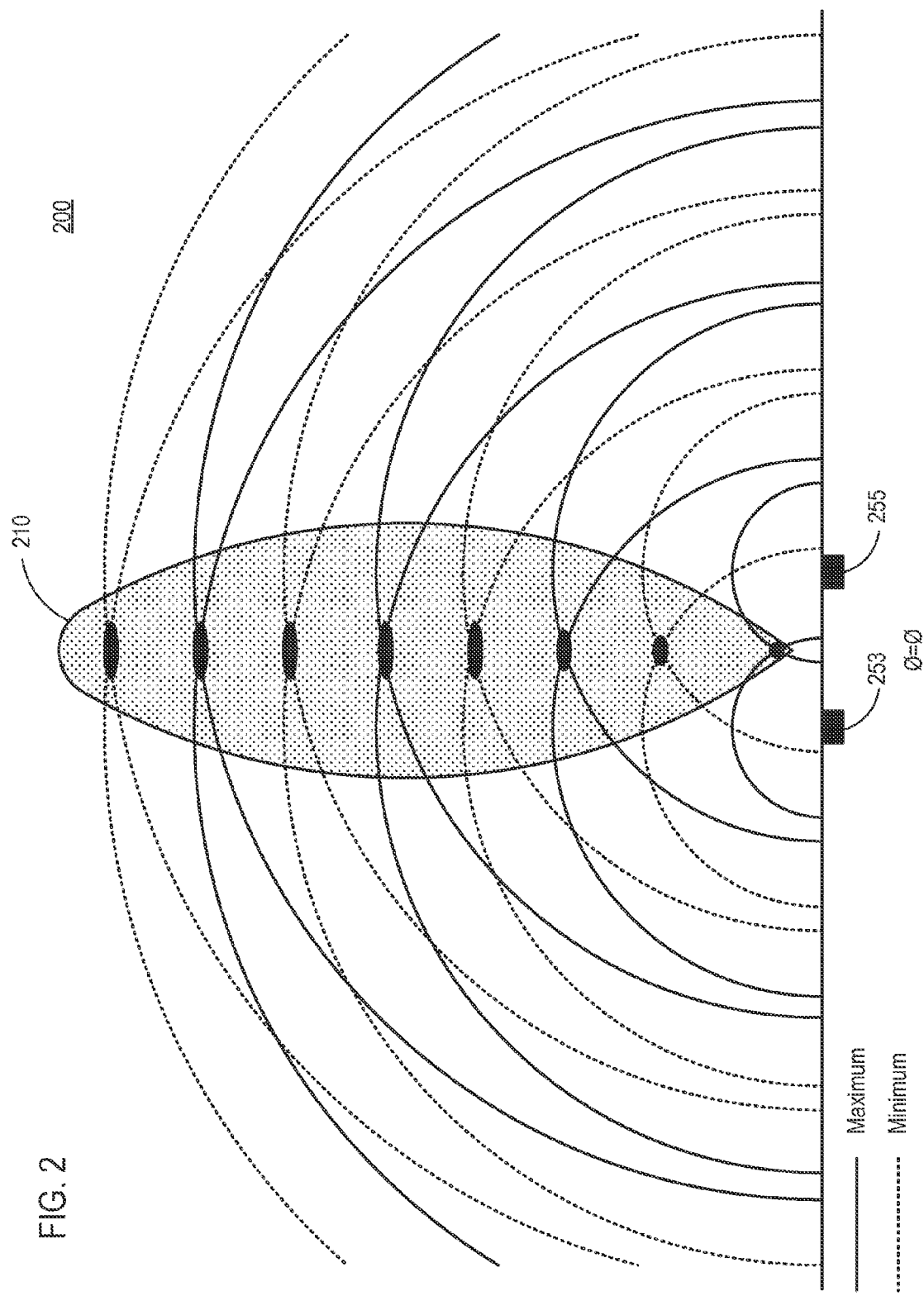
FIG. 2 illustrates a region of high-field strength in the interference pattern of the two electromagnetic radiation sources.

FIG. 2 illustrates a region of high-field strength 210 in the interference pattern 200 of two electromagnetic radiation sources 253 and 255. As illustrated the phase (Ø) of the first electromagnetic radiation source 253 may be equal to the phase (Ø) of the second electromagnetic radiation source 255. Similar to the previous embodiment in FIG. 1, solid lines and dashed lines concentric with the electromagnetic radiation sources 253 and 255 represent maximums and minimums, respectively, of the electromagnetic radiation sources 253 and 255, respectively.

According to various embodiments, the antinodes (shown as black ellipses) within the region of high-field strength 210 may have an attribute that makes the antinodes suitable for electroporation, either alone (i.e., the single antinode) or in combination with antinodes of one or more additional regions of high-field strength 210. In some embodiments (e.g., utilizing traveling waves) the antinodes may move throughout the volume, while remaining located within the region of high-field strength 210. In such embodiments, electroporation can occur within selected portions of the region of high-field strength 210. In embodiments utilizing standing waves, the spatial locations of antinodes may remain fixed at specific locations within the region of high-field strength 210, and may serve as electroporation sites.

Figure 3:
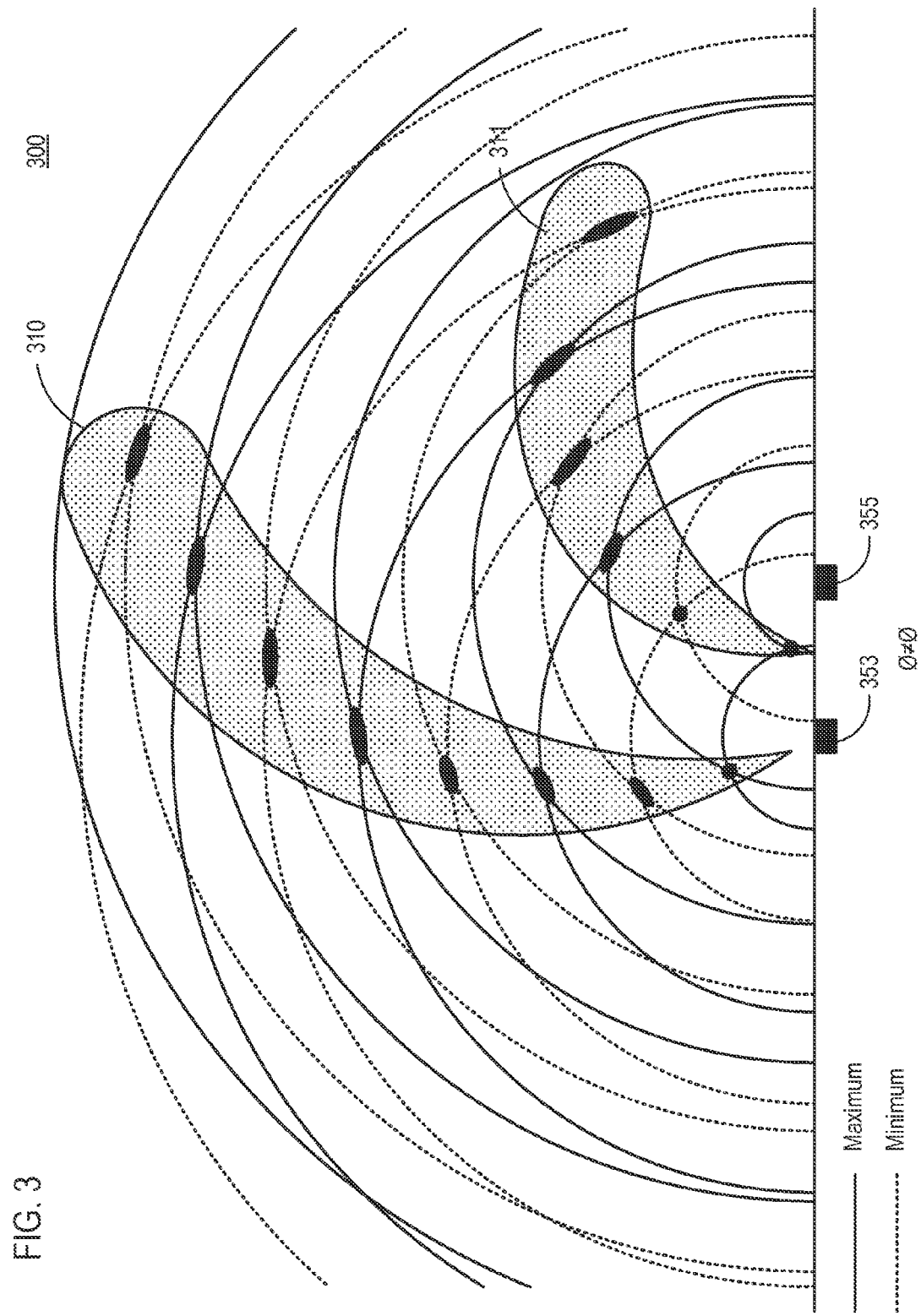
FIG. 3 illustrates the phase of one of the electromagnetic radiation sources delayed with respect to the other electromagnetic radiation source, and the resulting interference pattern.

FIG. 3 illustrates the phase (Ø) of a first electromagnetic radiation source 353 delayed with respect to phase (Ø) of the second electromagnetic radiation source 355. As illustrated, the resulting interference pattern 300 may include two regions 310 and 311 of relatively high-field strength. The first region 310 may have a higher field strength than the second region 311. In various embodiments, the antinodes within one or both of the regions 310 and 311 of relatively high-field strength may be suitable for electroporation. In some embodiments, only the antinodes within the first region 310 of high-field strength may be suitable to cause electroporation, whether alone or in combination (e.g., via constructive interference) with one or more additional regions 310 of high-field strength from one or more additional electromagnetic radiation sources.

As in the other embodiments, solid lines and dashed lines concentric with the electromagnetic radiation sources 353 and 355 represent maximums and minimums, respectively, of the electromagnetic radiation sources 353 and 355, respectively. As illustrated, by modifying the phase of one or both of the first and second electromagnetic radiation sources, the location of one or more antinodes within the region 310 of high-field strength are moved, as may be the shape and/or location of the region 310 of high-field strength itself. In various embodiments, a controller may selectively modify the phase of one or more of the electromagnetic radiation sources 353 and 355 to move the antinodes according to an electroporation pattern.

In various embodiments, each of the electromagnetic radiation sources 353 and 355 may be a distinct electromagnetic radiation generator. Accordingly, the controller may modify the phase and/or amplitude of one or more of the distinct electromagnetic radiation generators. In other embodiments, a single electromagnetic radiation generator may be used to create any number of electromagnetic radiation sources, including electromagnetic radiation sources 353 and 355. In such embodiments, the controller may adjust a phase of one or more of the electromagnetic radiation sources 353 and 355 using any of a wide variety of phase delay techniques, including through the use of various antennas, repeaters, lenses, reflective devices, deflective devices, modifications in the relative location of a lens, opening, cross slit, slit, aperture, and/or the like.

In some embodiments the controller may adjust an amplitude of one or more of the electromagnetic radiation sources 353 and 355 using any of a wide variety of techniques, including through the use of variable resonances (e.g., as done in metamaterial surface antenna technology), variable attenuation, variable amplification, and/or the like.

Figure 4:
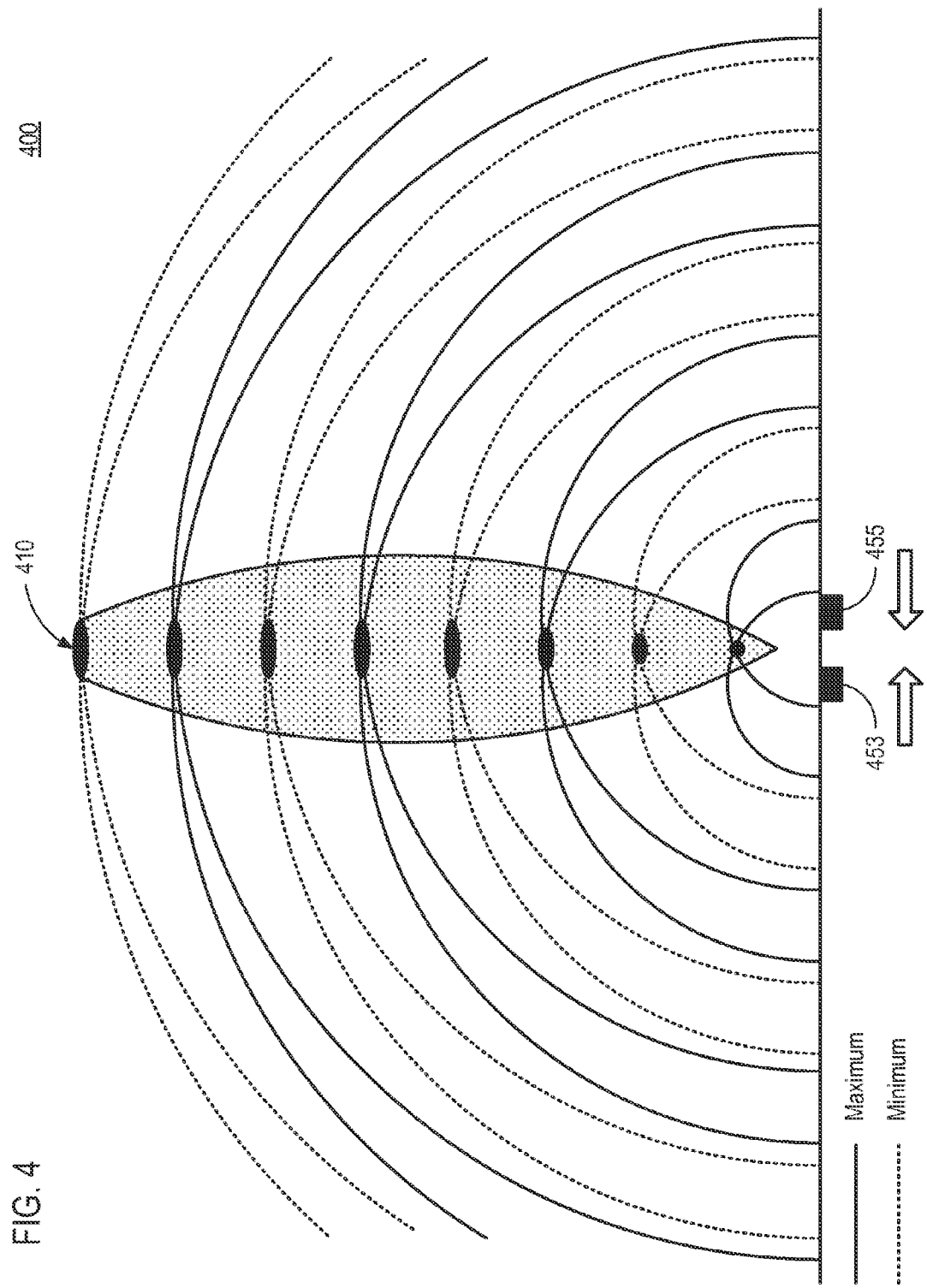
FIG. 4 illustrates the relatively narrow high-field strength region of the interference pattern as the two electromagnetic radiation sources are brought in closer proximity.

FIG. 4 illustrates the relatively tighter high-field strength region 410 of the interference pattern 400 as the two electromagnetic radiation sources 453 and 455 are brought into closer proximity. Accordingly, a controller may modify the location of one or both of the electromagnetic radiation sources 453 and/or 455 to modify the location and/or intensity of the antinodes within the region of high-field strength 410. The interference pattern 400 may cause a narrower and/or higher intensity region of high-field strength 410.

As in the previous embodiments, solid lines and dashed lines concentric with the electromagnetic radiation sources 453 and 455 represent maximums and minimums, respectively, of the electromagnetic radiation sources 453 and 455, respectively. In various embodiments, each of the electromagnetic radiation sources 453 and 455 may be a distinct electromagnetic radiation generator. Accordingly, the controller may modify the physical location of one or more of the distinct electromagnetic radiation generators.

In other embodiments, a single electromagnetic radiation generator may be used to create any number of electromagnetic radiation sources, including electromagnetic radiation sources 453 and 455. In such embodiments, the controller may adjust a physical location of one or more of the electromagnetic radiation sources 453 and 455 by adjusting the location of one or more antennas, repeaters, lenses, reflective devices, deflective devices, openings, cross slits, slits, apertures, and/or the like.

The movement of the electromagnetic radiation generator associated with one or more electromagnetic radiation sources may modify the relative physical location, phase, and/or magnitude of one or more of the electromagnetic radiation sources, including electromagnetic radiation sources 453 and 455.

FIGS. 5A through 5E represent various embodiments of possible electromagnetic radiation patterns using a plurality of electromagnetic radiation sources and/or generators at various separation distances, coplanar positions, non-coplanar positions, and/or phase delays. The illustrated embodiments of electromagnetic radiation patterns are merely provided as illustrative examples.

Any number of alternative electromagnetic radiation patterns using any number of electromagnetic radiation sources and/or electromagnetic radiation generators may be used in conjunction with the various systems and methods described herein. Furthermore, while FIGS. 5A-5E illustrate two-dimensional projections of electromagnetic radiation patterns, it should be understood that use of multiple electromagnetic radiation sources and/or electromagnetic radiation generators may be employed to form complex three-dimensional electromagnetic radiation patterns.

Moreover, the complex three-dimensional electromagnetic radiation patters may be varied in time as well, such that the three-dimensional electromagnetic radiation pattern varies over time according to a predetermined pattern, randomly, and/or based on a measured characteristic of the electromagnetic radiation, an object, volume, or surface being electroporated, a temperature, and/or other attribute associated with an electroporation system. One purpose of FIGS. 5A-5E is to show that the relative positioning and phase delays of a multi-source electromagnetic radiation system may be modified to control the relative intensity and/or position of regions of high-field strength.

Figure 5A:
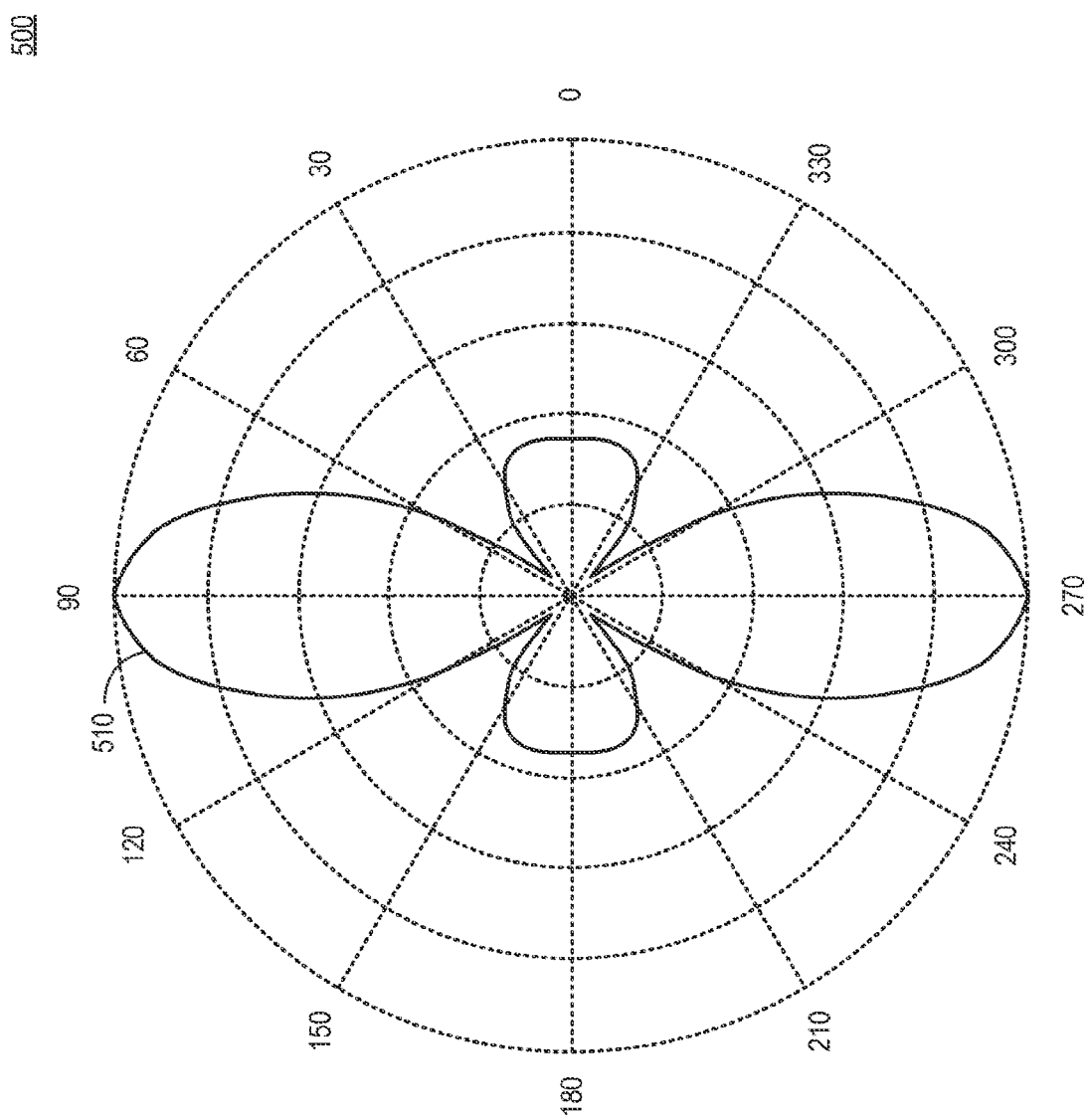
FIG. 5A illustrates a multi-source field strength pattern, according to one embodiment.

FIG. 5A illustrates a multi-source field strength pattern 500, according to one embodiment. The illustrated region 510 of high-field strength may be generated using three coplanar electromagnetic radiation sources with uniform spacing.

Figure 5B:
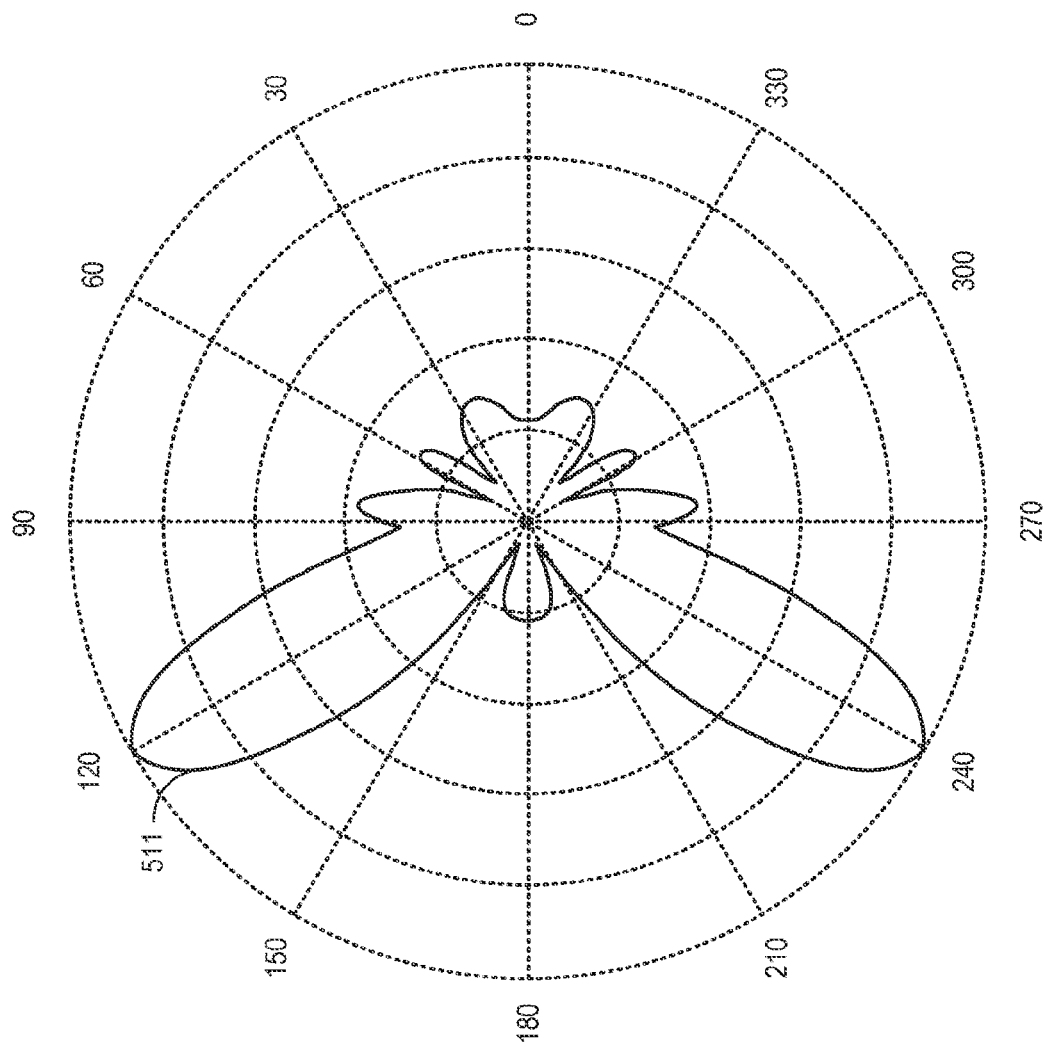
FIG. 5B illustrates a multi-source field strength pattern according to another embodiment.

FIG. 5B illustrates a multi-source field strength pattern 501 according to another embodiment. The illustrated region 511 of high-field strength may be generated using the same electromagnetic radiation sources used in FIG. 5A, but with a phase delay. Accordingly, it can be appreciated that a controller may adjust the phase delay of one or more electromagnetic radiation sources in a multi-source electromagnetic radiation system, to vary the direction of a primary lobe of a region 511 of high-field strength.

Figure 5C:
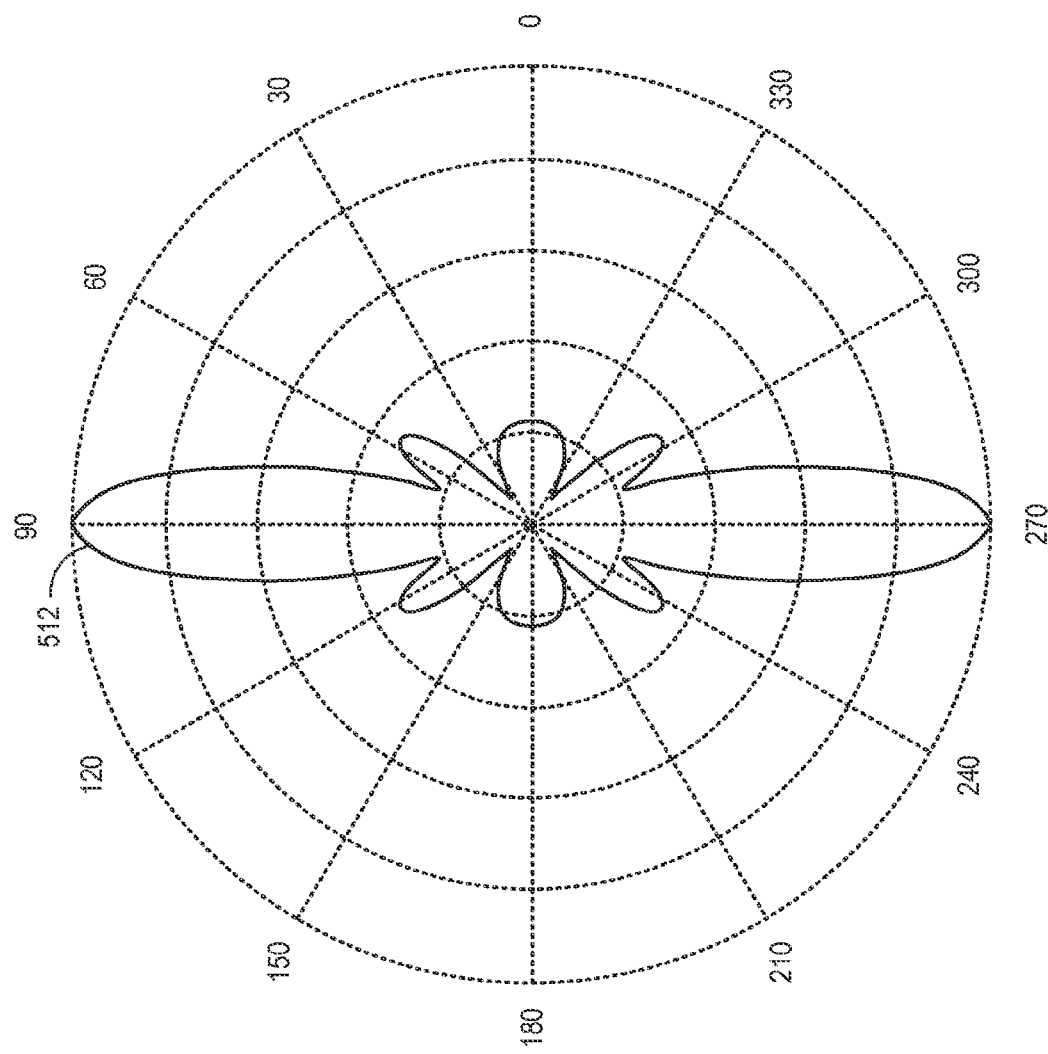
FIG. 5C illustrates a multi-source field strength pattern according to another embodiment.

FIG. 5C illustrates a multi-source field strength pattern 502 according to another embodiment. The illustrated embodiment includes a primary lobe of a region 512 of high-field strength narrower than that shown in FIGS. 5A and 5B. The narrower primary lobe of the region 512 of high-field strength, and additional secondary lobes, are created using five electromagnetic radiation sources in a coplanar and uniformly spaced arrangement. Similar to a comparison of FIGS. 5A and 5B, changing the phase and/or relative physical location of one or more of the electromagnetic radiation sources may modify the direction of the primary lobe(s) of the region 512 of high-field strength.

Figure 5D:
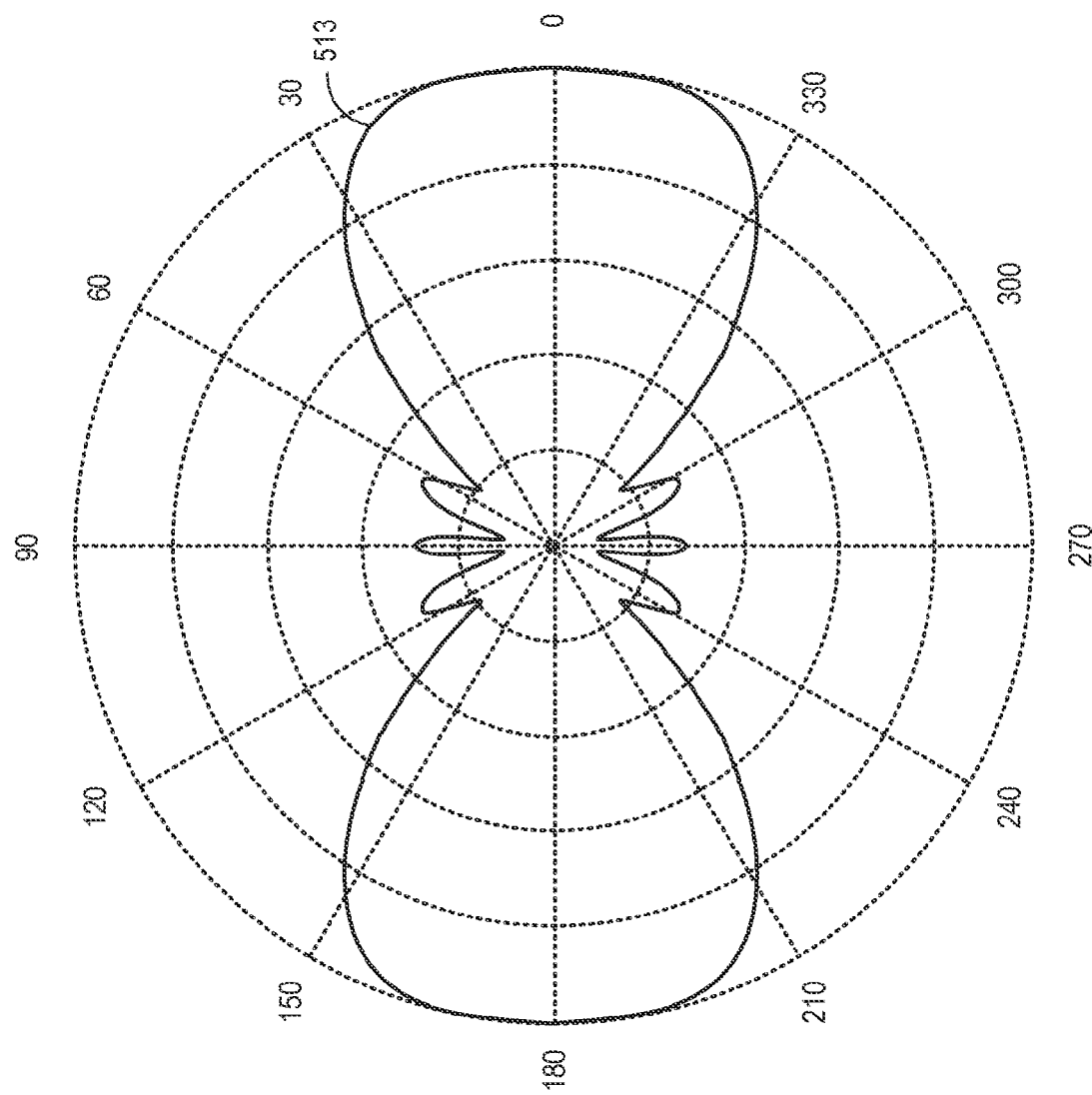
FIG. 5D illustrates a multi-source field strength pattern according to another embodiment.

FIG. 5D illustrates a multi-source field strength pattern 503 according to another embodiment. The illustrated embodiment with relatively wide primary lobes of the region of high-field strength 513 may be generated by delaying the phase of one or more of the electromagnetic radiation sources used to generate the region 512 of high-field strength in FIG. 5C.

As illustrated, in FIG. 5E a different phase delay of one or more of the electromagnetic radiation sources used to generate the region 512 of high-field strength in FIG. 5C may only slightly widen the primary lobes of the region 514 of high-field strength.

As illustrated in the examples provided in conjunction with FIGS. 5A-5E, a controller may modify the number of electromagnetic radiation sources, the number of electromagnetic radiation generators, the physical location of one or more of the electromagnetic radiation sources and/or generators, and/or to a characteristic, such as the phase, magnitude, frequency, etc., of one or more of the electromagnetic radiation sources and/or electromagnetic radiation generators to vary the physical location of one or more antinodes (i.e., the antinode(s) within the region(s) of high-strength electric field). In some embodiments, the controller may comprise a network of disparate sub-controllers for controlling various characteristics and components of a multi-source and/or multi-generator system.

Figure 6A:
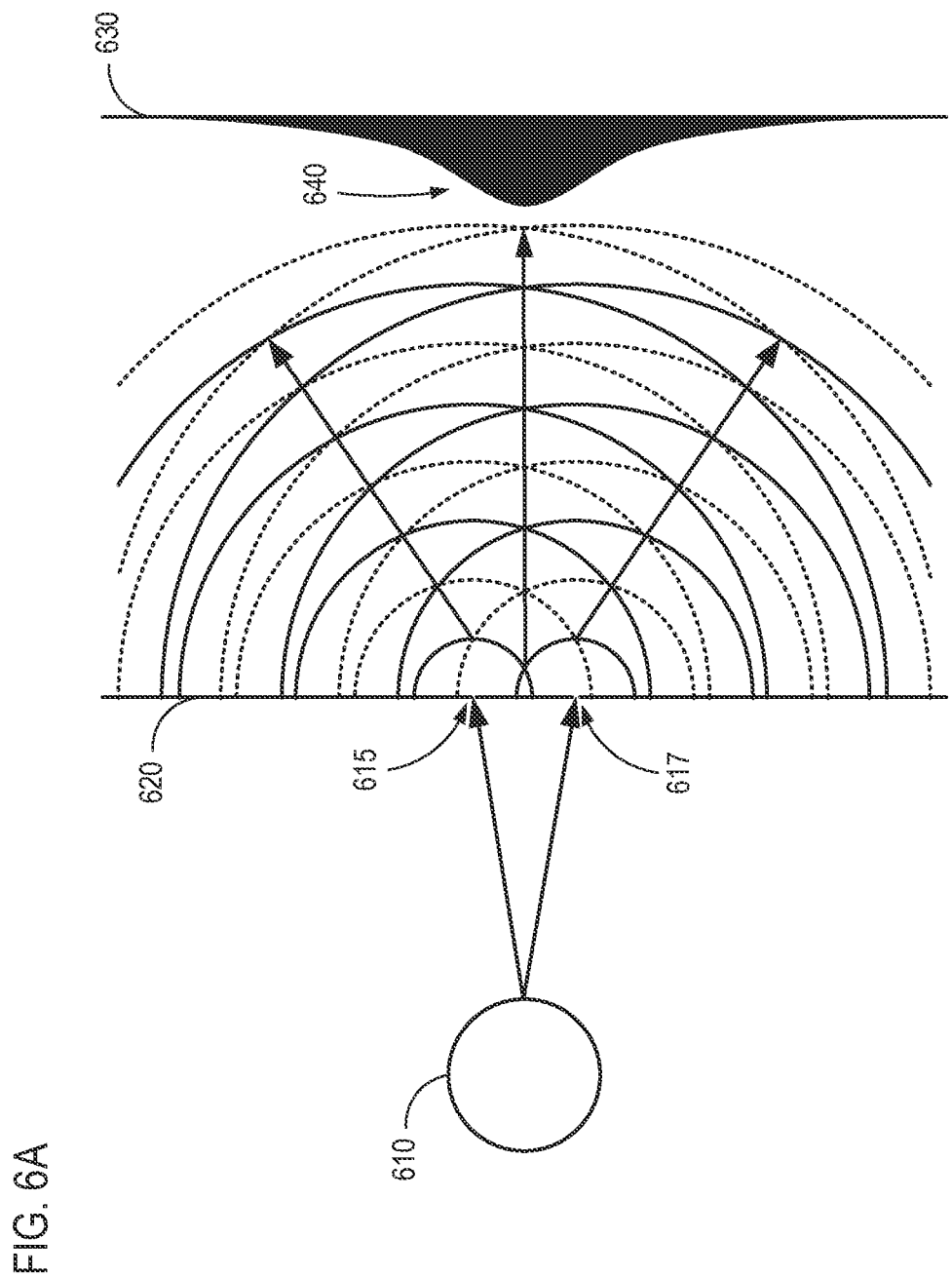
FIG. 6A illustrates a single electromagnetic radiation generator used in combination with a perforated surface to create multiple electromagnetic sources.

FIG. 6A illustrates a single electromagnetic radiation generator 610 used in combination with a perforated surface 620 to create multiple electromagnetic radiation sources 615 and 617. As can be appreciated, due to the wave particle duality of electromagnetic radiation, apertures, slits, cross slits, spiral openings, and/or other perforations (collectively referred to as "slits") may each be used to create a unique electromagnetic radiation source 615 and 617 based on a single electromagnetic radiation generator 610. Accordingly, an interference pattern, similar to those shown in FIGS. 1-5E or a different interference pattern may be created using one or more electromagnetic radiation generator(s) 610 in combination with one or more slits (or the like).

According to various embodiments, one or more electromagnetic radiation sources may be used to generate an interference pattern with one or more antinodes. In some embodiments, a single electromagnetic radiation generator 610 may be used in combination with one or more slits, reflective elements, refractive elements, apertures, and/or the like to create at least one electroporating antinode within an interference pattern. The interference pattern created may be dependent on various factors, including the frequency of the electromagnetic radiation, the amplitude of the electromagnetic radiation, the relative positioning of the slits, the relative phase delay caused by each slit (e.g., in the case of a refractive for phase-delaying element such as an antenna or repeater), the relative spacing of the slits, etc.

A single electromagnetic radiation 610 generator may supply each electromagnetic radiation source 615 and 617 (e.g., a point source or an approximate point source) with electromagnetic radiation. In other embodiments, multiple electromagnetic radiation generators may supply multiple electromagnetic radiation sources with electromagnetic radiation. Accordingly, the number of electromagnetic radiation generators and the number of electromagnetic radiation sources may be a 1:1 mapping, a 1:N mapping, or an N:M mapping, where N and M are integers greater than 0.

Figure 6B:
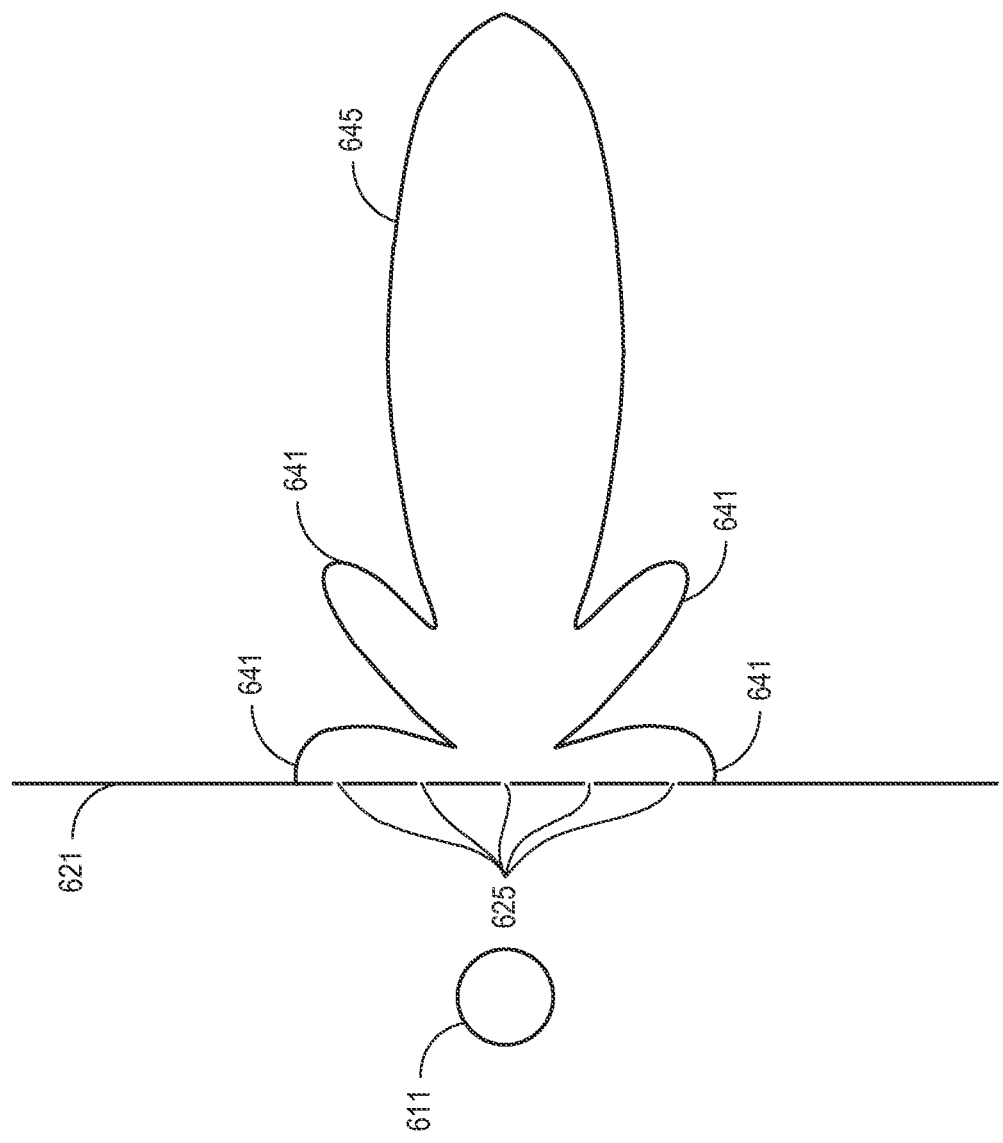
FIG. 6B illustrates a perforated surface used to create a multi-source electromagnetic interference pattern with a primary lobe.

FIG. 6B illustrates a perforated surface 621 used to create a multi-source electromagnetic interference pattern with a primary lobe 645. In the illustrated embodiment, a single electromagnetic radiation generator 611 is used in combination with a perforated surface 621 to create five electromagnetic radiation sources 625. The five coplanar sources 625 are used to generate an interference pattern with a primary lobe 645 of high-field strength and several secondary lobes 641 of high-field strength. One or more attributes of the antinode(s) within the primary lobe 645 may make the antinode suitable for electroporation. In some embodiments, the primary lobe 645 may be combined (via constructive interference) with the primary lobe(s) of one or more additional electromagnetic radiation patterns to generate an antinode suitable for electroporation.

Figure 7:
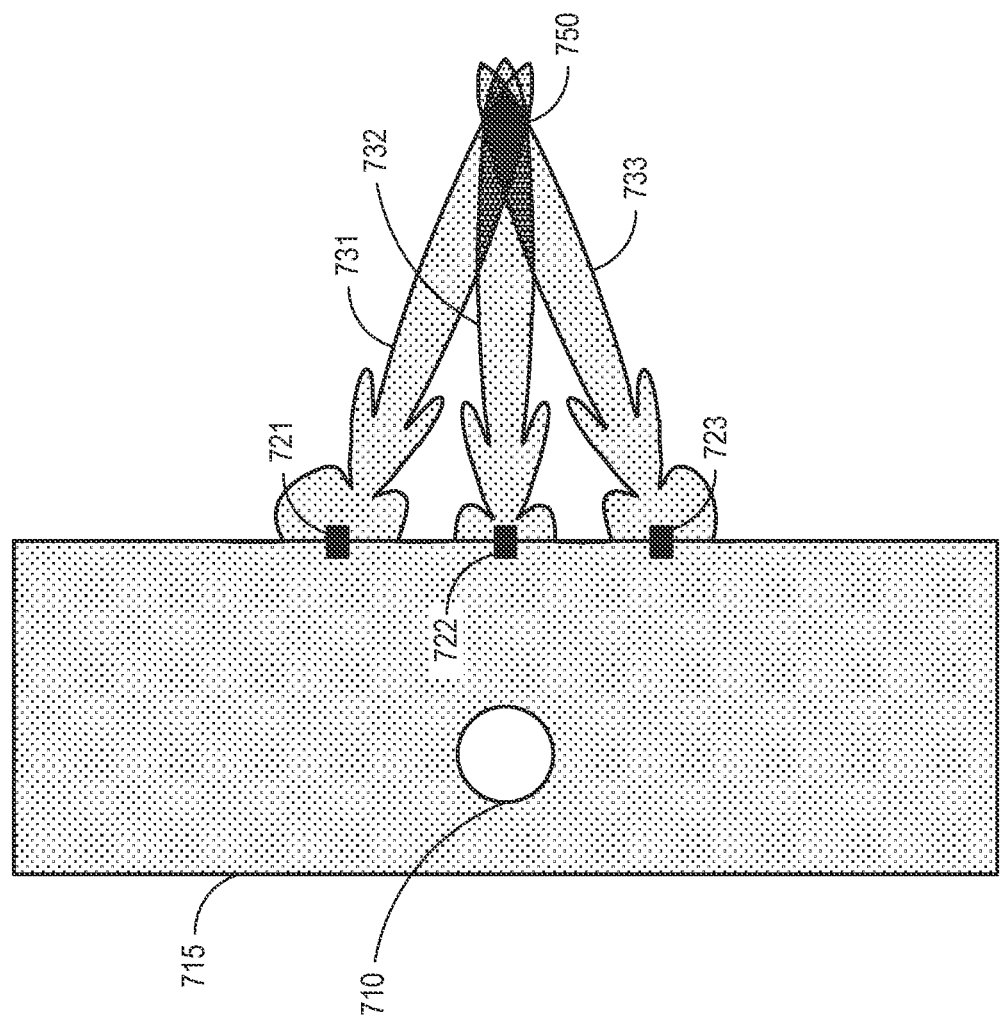
FIG. 7 illustrates a plurality of electromagnetic radiation sources used to create electromagnetic radiation patterns with overlapping primary lobes.

FIG. 7 illustrates a plurality of electromagnetic radiation sources 721, 722, and 723 used to create electromagnetic radiation patterns 731, 732, and 733 with overlapping primary lobes. Constructive interference of the overlapping primary lobes may generate an antinode 750 with a sufficiently high-field strength and/or additional attributes to render the antinode suitable for electroporation. Specifically, the antinode 750 may be suitable for irreversible electroporation for sterilization by rendering cells non-viable that come into contact with the antinode for a sufficient duration.

In various embodiments, each of the radiation sources 721, 722, and 723 may receive electromagnetic radiation from a common electromagnetic radiation generator 710. In other embodiments, the number of electromagnetic radiation generators and the number of electromagnetic radiation sources may be a 1:1 mapping, a 1:N mapping, or an N:M mapping, where N and M are integers greater than 0.

In the illustrated embodiment, a region 715 may reflect and/or transmit electromagnetic radiation from the electromagnetic radiation generator 710 to each of the electromagnetic radiation sources 721, 722, and 723. Each electromagnetic radiation source 721, 722, and 723 may comprise a slit, aperture, cross slit, spiral slit, reflective element, refractive element, antenna, conformal antenna, metamaterial antenna, parabolic reflector, deflective element, repeater, phase delayer, and/or other electromagnetic radiation manipulation component.

By adjusting various characteristics of each of the electromagnetic radiation sources 721, 722, 723, such as a distance, location, phase, magnitude, beam-forming direction, etc., the location of the electroporating antinode 750 may be moved. As may be appreciated by one of skill in the art, the electroporating antinode may be moved (i.e., spatially varied) relative to the illustrated location by varying any one or more of a wide variety of characteristics of each of the electromagnetic radiation sources 721, 722, and 723.

In some embodiments, a controller may merely modify the direction of an antenna, while in other embodiments, the controller may use a spatial variation device to vary the phase of the generated electromagnetic radiation, utilize one or more refractive and/or reflective elements, move the volume with respect to the radiation sources, and/or move the radiation sources with respect to the object.

Thus, in various embodiments, an electroporating system may include one or more electromagnetic radiation generators and/or radiation sources, a spatial variation device as described herein, and a controller to control the relative spatial variation of the at least one antinode according to an electroporation pattern configured to regulate the generation of heat within a volume during sterilization.

Figure 8:
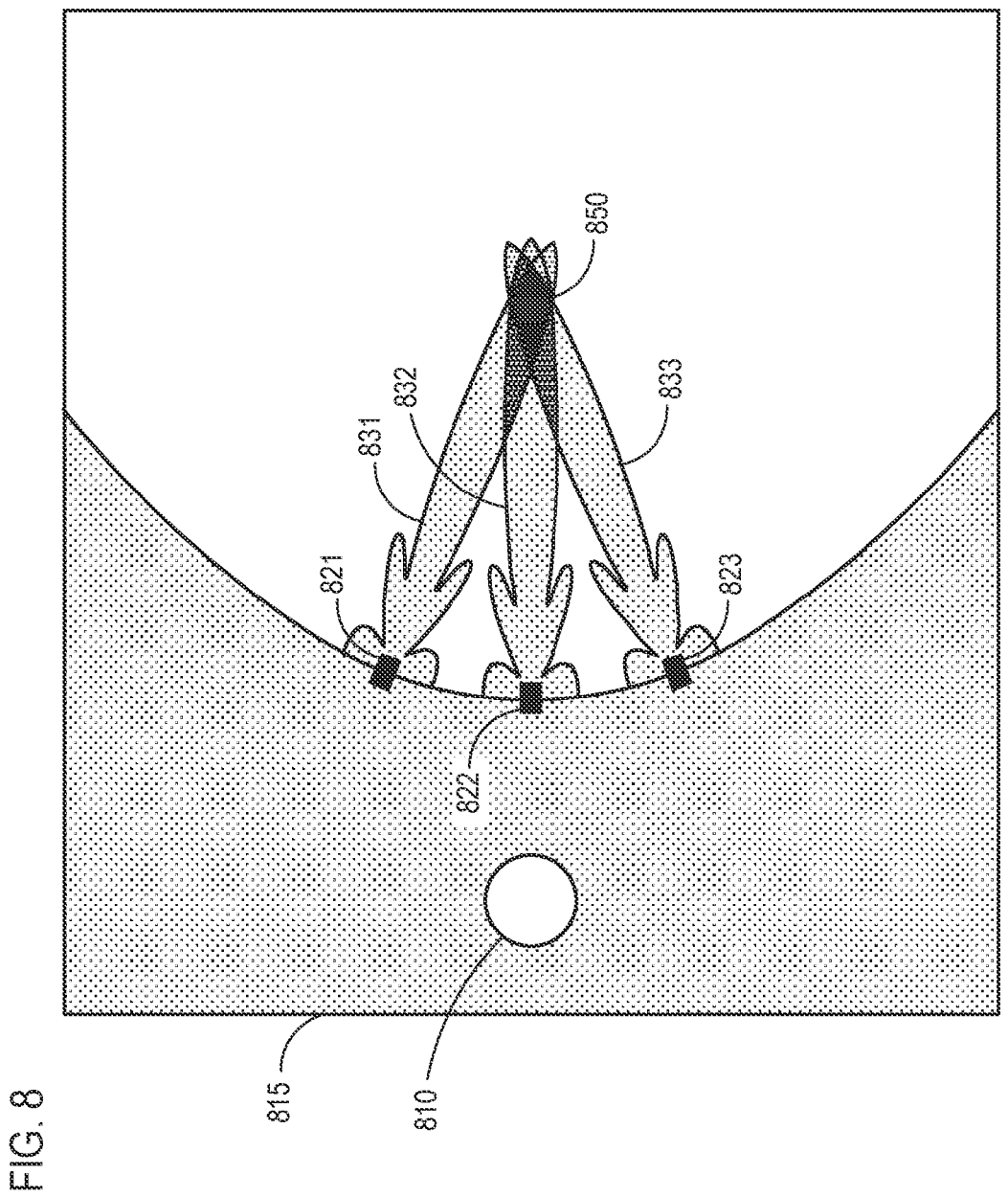
FIG. 8 illustrates a plurality of electromagnetic radiation sources along a curved surface used to create electromagnetic radiation patterns with overlapping primary lobes.

FIG. 8 illustrates a plurality of electromagnetic radiation sources 821, 822, and 823 along a curved surface of a region 815. A common electromagnetic radiation generator 810 may be utilized in some embodiments. In other embodiments, multiple electromagnetic radiation generators may be utilized. As in FIG. 7, an electroporating system 800 may include a plurality of electromagnetic radiation sources 821, 822, and 823 to create electromagnetic radiation patterns 831, 832, and 833 with overlapping primary lobes. Constructive interference of the overlapping primary lobes may generate an antinode 850 with a sufficiently high-field strength and/or additional attributes to render the antinode suitable for electroporation. Specifically, the antinode 850 may be suitable for irreversible electroporation for sterilization by rendering cells non-viable that come into contact with the antinode for a sufficient duration of time.

In various embodiments, each of the radiation sources 821, 822, and 823 may receive electromagnetic radiation from a common electromagnetic radiation generator 810. In other embodiments, the number of electromagnetic radiation generators and the number of electromagnetic radiation sources may be a 1:1 mapping, a 1:N mapping, or an N:M mapping, where N and M are integers greater than 0. Thus, while only three electromagnetic patterns 831, 832, and 833 (each having a primary lobe) are shown, it will be appreciated that any number of primary lobes may be made to intersect to create one or more antinodes suitable for sterilization via electroporation.

In the illustrated embodiment, a region 815 may reflect and/or transmit electromagnetic radiation from the electromagnetic radiation generator 810 to each of the electromagnetic radiation sources 821, 822, and 823. Each electromagnetic radiation source 821, 822, and 823 may comprise multiple slits, apertures, cross slits, spiral slits, reflective elements, refractive elements, antennas, conformal antennas, metamaterial antennas, parabolic reflectors, deflective elements, repeaters, phase delayers, and/or other electromagnetic radiation manipulation components.

A controller or spatial variation device in communication with a controller may move the physical location of the electroporating antinode 850 by adjusting various characteristics of one or more of the electromagnetic radiation sources 821, 822, 823, such as a distance, location, phase, magnitude, beam-forming direction, etc.

In some embodiments, a controller may merely modify the direction of an antenna, while in other embodiments, the controller may use a spatial variation device to vary the phase of the generated electromagnetic radiation, utilize one or more refractive and/or reflective elements, move the volume with respect to the radiation sources, and/or move the radiation sources with respect to the object.

Figure 9:
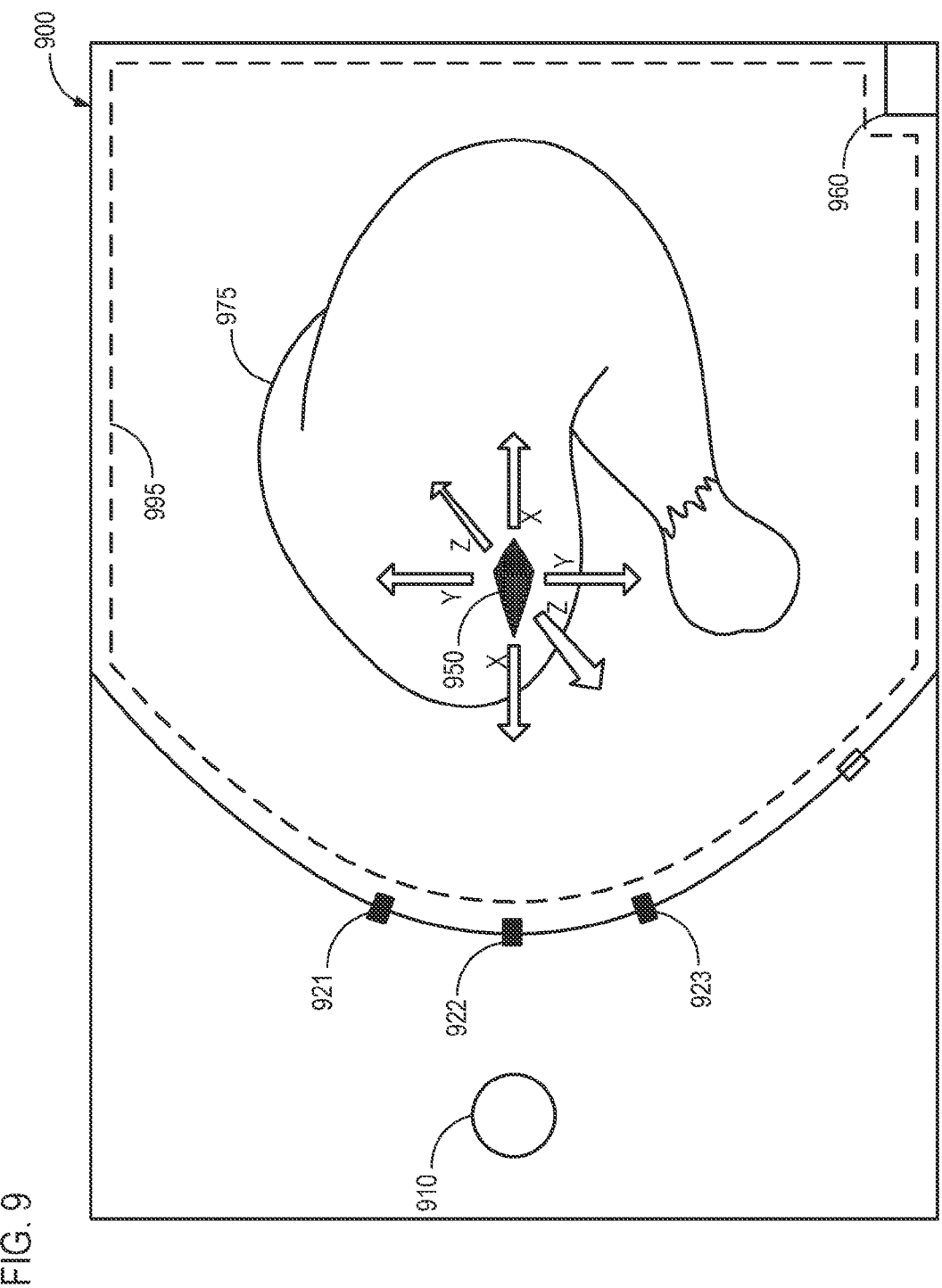
FIG. 9 illustrates an antinode corresponding to overlapping primary lobes of a plurality of electromagnetic radiation sources.

FIG. 9 illustrates an antinode 950 corresponding to overlapping primary lobes (not shown) of a plurality of electromagnetic radiation sources 921, 922, and 923. Again, the electromagnetic radiation sources 921, 922, and 923 may share a common electromagnetic radiation generator 910 and/or may receive electromagnetic radiation from additional and/or distinct electromagnetic radiation generators.

The electroporating antinode 950 may comprise a volume having dimensions associated with the boundaries at which the antinode 950 does not have a sufficiently high-field strength to reliably cause electroporation. Accordingly, the electroporating antinode volume 950 may be moved (relatively speaking, e.g., the object may be moved additionally or alternatively) relative to an object 975 to be electroporated. In some embodiments, the electroporating antinode volume 950 may be moved according to an electroporation pattern configured to regulate the generation of heat within the object 975.

In some embodiments, the electroporation pattern may be modified to include a cooling period and/or to avoid adjacent locations on the object to maintain a temperature of the object below a heating threshold. In some embodiments, a controller may implement a stochastic electroporation pattern, such that the antinode 950 is moved (relatively speaking) to random locations while still electroporating the entire object 975. In some embodiments, the controller may implement a rasterized electroporation pattern, such that the antinode 950 sequentially overlaps various regions of the object 975. The controller may implement a multi-pass electroporation pattern, such that the antinode 950 passes over at least some locations more than one time. One or more attributes of the antinode 950 may be varied between successive passes. In some embodiments, electroporation may be paused during a rest period between successive passes. In some embodiments, the controller may implement a Moiré pattern having one or more antinodes 950 for electroporating the object 975. A controller may automatically determine an appropriate electroporation pattern and/or allow a user to select from a variety of electroporation patterns.

A sensor(s) 960 may be configured to determine one or more temperatures associated with the electroporating antinode 950 and/or one or more portions of the object 975. The sensor(s) 960 may alternatively or additionally be used to determine a model, size, dimensions, composition, and/or other characteristic of the object 975. For example, the sensor(s) 960 may be in communication with a controller and configured to aid in the determination of a two-dimensional projection of the three-dimensional object 975. The sensor(s) 960 may therefore by useful for determining an electroporation pattern as well as maintaining a temperature characteristic (e.g., an absolute temperature, a relative temperature, and/or a rate of temperature change) within a range, below a threshold value, and/or above a threshold value.

In some embodiments, a region 900 for electroporating the object 975 may have a reflective and/or absorbing layer 995 to prevent and/or reduce the amount of stray electromagnetic radiation leaving the region 900.

Figure 10:
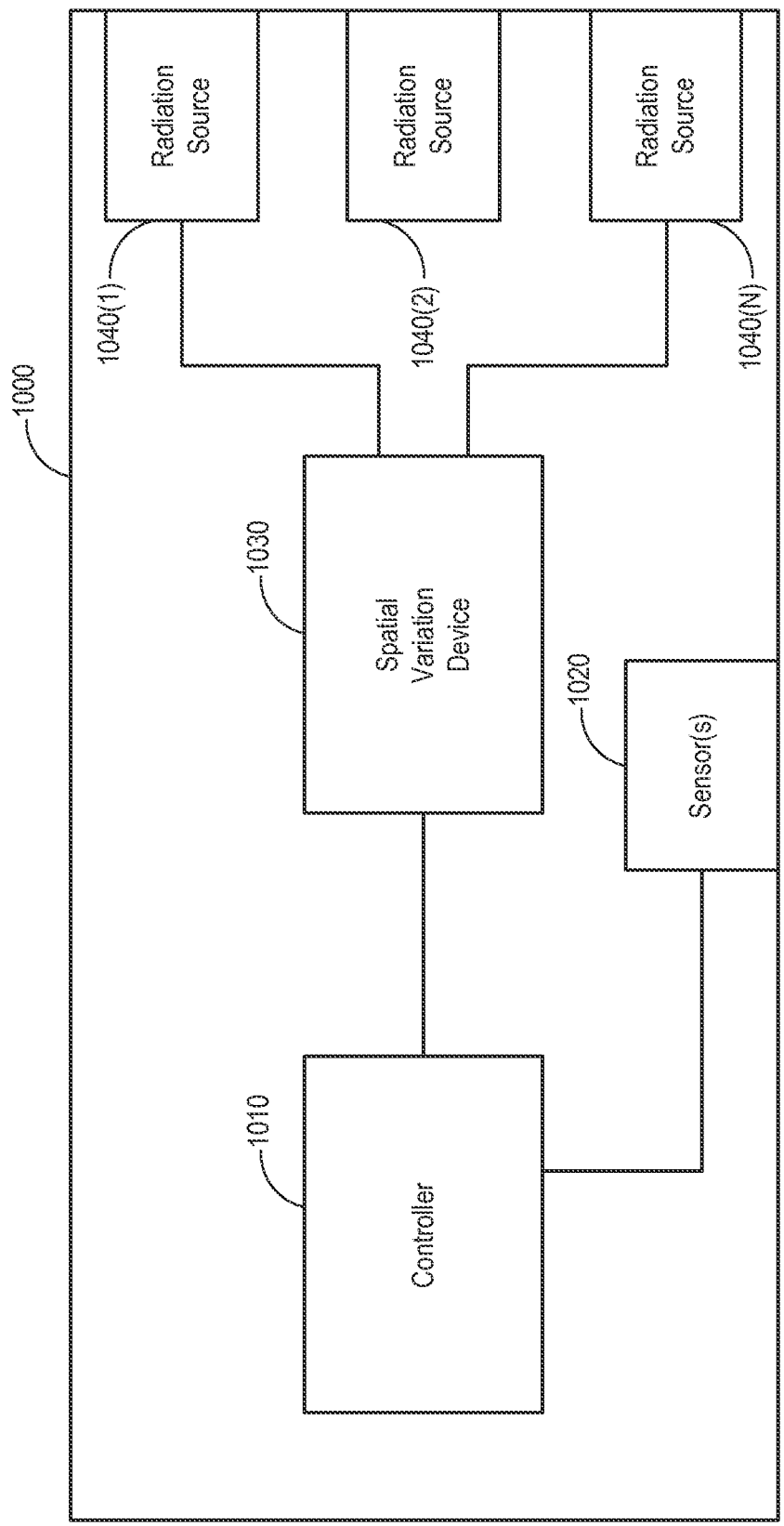
FIG. 10 illustrates a block diagram of a system for non-thermal electromagnetic sterilization.

FIG. 10 illustrates a block diagram of a system 1000 for non-thermal electromagnetic sterilization. In the illustrated embodiment, a plurality of radiation sources 1040(1), 1040(2), . . . 1040(N), where N is a positive integer, may be used to create at least one antinode suitable for electroporating an object and/or volume. The electromagnetic radiation sources 1040(1), 1040(2), . . . 1040(N) may be in communication with a spatial variation device 1030.

The spatial variation device 1030 may be configured to vary the phase of the electromagnetic radiation, utilize one or more refractive and/or reflective elements, move the volume with respect to the radiation sources, and/or move the radiation sources with respect to the object.

In some embodiments, the spatial variation device 1030 may be configured to move one or more radiation generators, modify one or more slits/apertures functioning as radiation point/line/cross sources, and/or varying a phase of one or more of the electromagnetic radiation generators and/or electromagnetic radiation sources. Alternatively or additionally, the spatial variation device 1030 may move an object to be electroporated with respect to the electroporating antinode. Again, although the electroporating antinode is described as electroporating a volume or object, it is appreciated that a surface may be electroporated instead of or in addition to a volume.

One or more sensors 1020 may be utilized to determine one or more temperatures of an object to be electroporated and/or of an object during electroporation. The sensors 1020 may alternatively or additionally be used to determine a model, size, dimensions, composition, and/or other characteristic of the object to be electroporated. For example, the sensors 1020 may be in communication with a controller 1010 and configured to aid in the determination of a two-dimensional projection of the three-dimensional object to be electroporated. The sensors 1020 may therefore be useful for determining an electroporation pattern as well as maintaining a temperature characteristic (e.g., an absolute temperature, a relative temperature, and/or a rate of temperature change) within a range, below a threshold value, and/or above a threshold value.

A controller 1010 may act as an intermediary between the various other components, 1020, 1030, and 1040(1), 1040(2), ... 1040(N). The controller may determine an electroporation pattern for moving (relatively speaking) the at least one antinode. The controller may ensure that a specific sterilization level is met and/or that a temperature range (absolute, relative, or rate) is maintained during electroporation. The controller 1010 may be implemented in software, hardware, and/or firmware. In various embodiments, the components 1010, 1020, 1030, and 1040(1), 1040(2), ... 1040(N) may be in disparate locations, be individual devices, be incorporated as sub-portions of other devices, be in wireless communication, and/or be in wired communication. The controller 1010 may be a cloud-based controller in communication with the spatial variation device 1030 and/or the sensors 1020.

FIG. 11A illustrates a non-thermal electroporation system 1110 configured to sterilize a room 1100. As illustrated, a plurality of electromagnetic radiation sources 1111, 1112, and 1113 may each create a beam-formed electromagnetic radiation pattern 1131, 1132, and 1133. Constructive interference of the electromagnetic radiation beam-formed electromagnetic radiation patterns 1131, 1132, and 1133 may create at least one antinode 1150 with a sufficiently high-field strength to cause electroporation.

Specifically, the antinode 1150 may be adapted to cause irreversible electroporation and render cells un-viable, thereby at least partially sterilizing objects and/or volumes. By varying the location of the antinode 1150 and/or the duration of time in each location, the non-thermal electroporation system 1110 may be used to sterilize the room 1100. A controller and/or spatial variation device within the non-thermal electroporation system 1110 may be used to move the antinode 1150 according to one or more electroporation patterns.

The electroporation pattern may be adapted to regulate the generation of heat within the room 1100 and/or within objects and/or surfaces within the room 1100. The electroporation pattern may alternatively or additionally be adapted to ensure a specific sterilization threshold is achieved for at least a portion (possibly all) of the room 1100. In some instances, portions of the room 1100 may not be sterilizable. The non-thermal electroporation system 1110 may be configured to notify a user of un-sterilizable locations and/or of deviations from the regulated temperature characteristics.

Figure 11B:
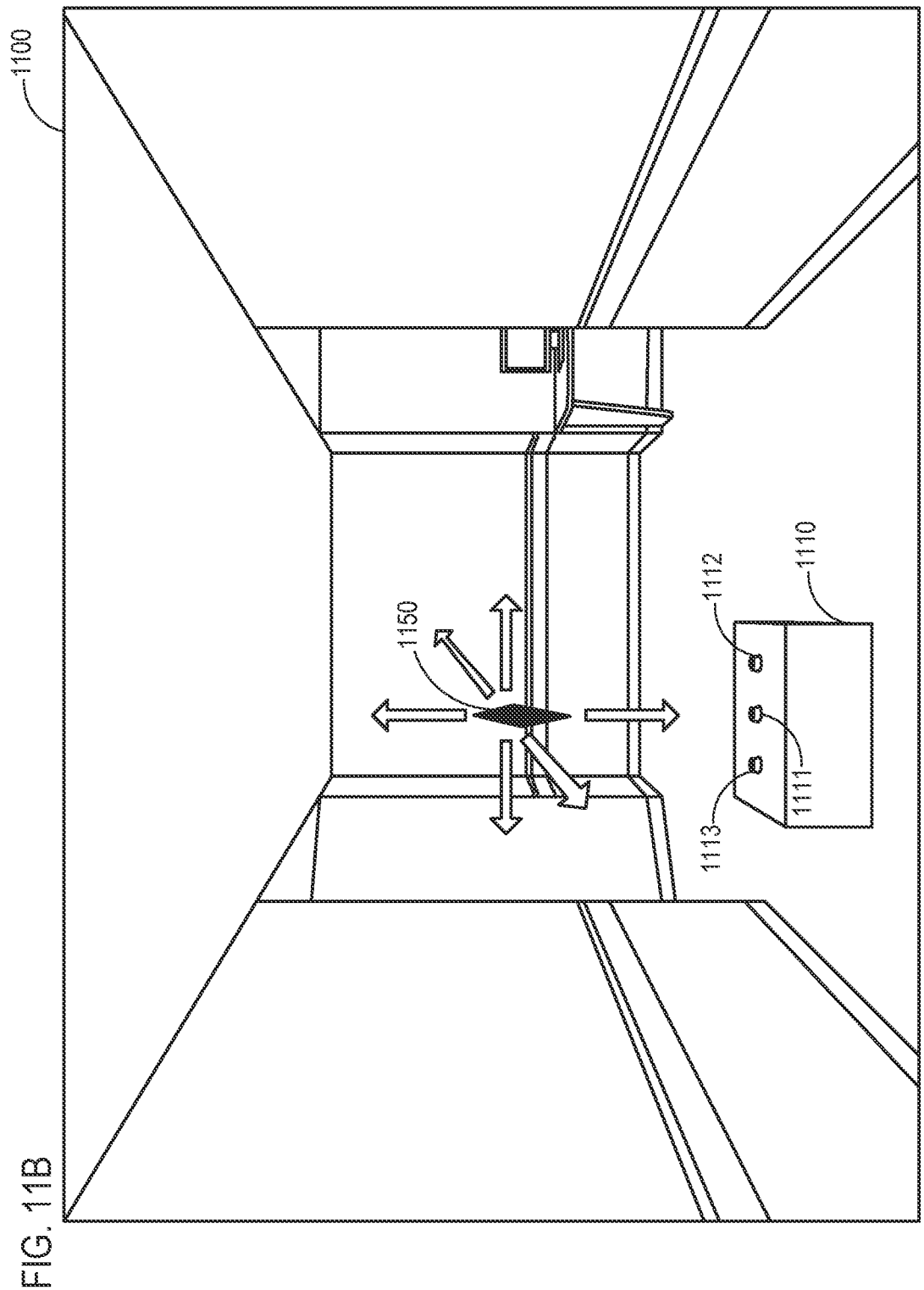
FIG. 11B illustrates potential directional movement of an electroporating antinode created by the non-thermal electroporation system for sterilizing the room.

FIG. 11B illustrates potential directional movement of an electroporating antinode 1150 created by the non-thermal electroporation system 1110 for sterilizing the room 1100. Again, an electroporation pattern, such as a rasterizing pattern or a stochastic pattern, may be utilized. In such embodiments, the antinode 1150 may be kept energized during movement, pulsed on and off during movement, and/or disabled during movement.

Figure 12:
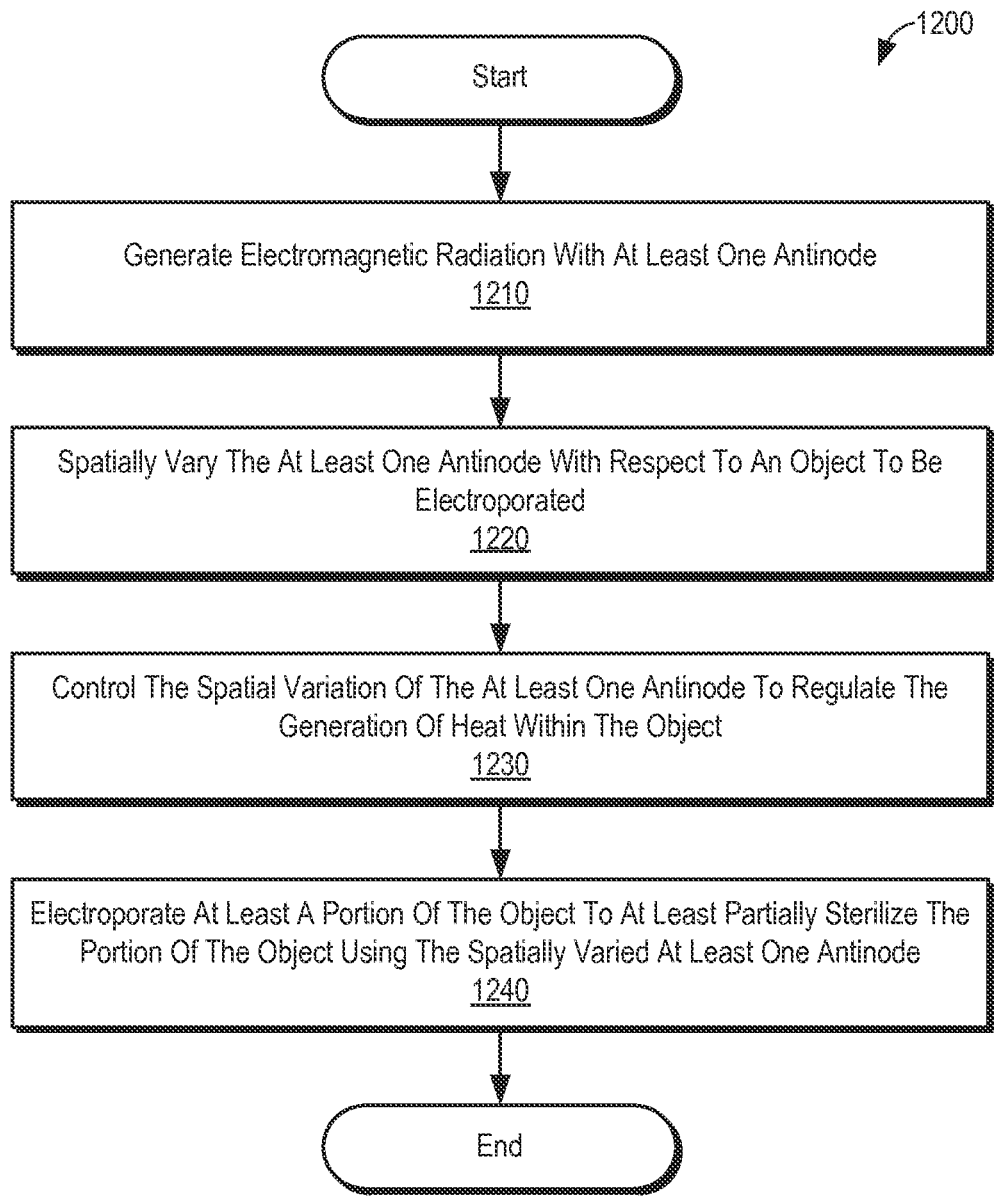
FIG. 12 illustrates a method for non-thermal sterilization via high-peak-field electroporation.

FIG. 12 illustrates a method 1200 for non-thermal sterilization via high-peak-field electroporation. As illustrated, electromagnetic radiation may be generated 1210 with at least one antinode. The generated electromagnetic radiation may be generated using a single electromagnetic radiation generator, via multiple electromagnetic radiation sources in communication with one or more electromagnetic radiation generators, and/or in another manner. The at least one antinode may refer to the one or more antinodes in a high-field region of a beam-formed electromagnetic radiation transmission and/or the constructive interference pattern of one or more electromagnetic radiation sources and/or the overlap of two or more primary lobes of various electromagnetic radiation sources, as described herein.

The at least one antinode may be suitable for sterilization via electroporation. A controller or spatial variation device (possibly in communication with the controller) may spatially vary 1220 the at least one antinode with respect to an object to be electroporated. In some embodiments, this may comprise moving the absolute location of the at least one antinode. In other embodiments, this may comprise moving the absolute location of the object and/or the absolute location of the at least one antinode.

The controller may control 1230 the spatial variation of the at least one antinode to regulate the generation of heat within the object. In various embodiments, one or more temperatures associated with the volume may be monitored. In some embodiments, it may be desirable to maintain the temperature of a volume below a specific threshold and/or maintain a rate of temperature increase (or decrease) below (or above) a threshold.

In some embodiments, the electromagnetic radiation may be generated in pulses and the power, frequency, pulse length, pulse spacing, pulse duty factor, and/or pulse shape may be adjusted responsive to a measured temperature associated with a volume. A controller may vary one or more attributes of the electromagnetic radiation, such as a pulse length, a pulse spacing, a pulse duty factor, a pulse shape, and/or other characteristic.

In some embodiments, the electroporation pattern may be modified to include a cooling period and/or to avoid adjacent locations on the object to maintain a temperature of the object below a heating threshold. In some embodiments, a controller may implement a stochastic electroporation pattern, such that the antinode is moved (relatively speaking) to random locations while still electroporating the entire volume. In some embodiments, the controller may implement a rasterized electroporation pattern, such that the antinode sequentially overlaps various regions of the volume. The controller may implement a multi-pass electroporation pattern, such that the antinode passes over at least some locations more than one time. One or more attributes of the antinode may be varied between successive passes. In some embodiments, electroporation may be paused during a rest period between successive passes. In some embodiments, the controller may implement a Moiré pattern having one or more antinodes for electroporating the volume. A controller may automatically determine an appropriate electroporation pattern and/or allow a user to select from a variety of electroporation patterns.

In some embodiments, the electroporating antinode(s) may be caused by the constructive interference of one or more intersecting beam-formed electromagnetic radiation patterns. The antinode may electroporate the object to achieve a specific amount of sterilization. The specific amount of sterilization may be measured by an intensity of the electric field and/or a time of exposure to the electric field. The time of exposure may correspond to the intensity of the electric field. The specific amount of sterilization may correspond to a composition of the object where different compositions are sterilized to different degrees. The specific amount of sterilization may also correspond to a known type of bacteria or other sterilizable entity. In various embodiments, each electroporated region of a volume to be electroporated may be subjected to a minimum intensity of an electric field for a particular amount of time. The amount of time may vary inversely with the intensity of the electric field. The time and/or intensity for electroporation may be determined using one or more sensors and may be associated with a type of volume/object being electroporated, the type of cell desired to kill, the color of the object, the mass of the object, the shape of the object, and/or other characteristic of the object being sterilized.

Ultimately, the electroporating antinode may be used to electroporate 1240 at least a portion of the object. The electroporation of the portion of the object may include irreversible electroporation, such that the portion of the object is at least partially sterilized using the at least one antinode.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

This disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A system for electroporation, the system comprising:
   a plurality of microwave electromagnetic (EM) radiation sources configured to generate microwave EM radiation with an interference pattern having at least one antinode within a region, wherein an attribute of an electric field associated with the at least one antinode is sufficient to cause electroporation of a cell wall;
   a spatial variation device configured to vary a location of the at least one antinode with respect to the region, wherein at least a portion of an object is configured to be at least partially sterilized via the electroporation where the at least one antinode overlaps the object; and
   a controller configured to control the spatial variation device to spatially vary the at least one antinode according to an electroporation pattern configured to regulate a sterilization within the portion of the object and maintain a temperature of the portion of the object below a sterilization temperature.

2. The system of claim 1, wherein the spatial variation device is configured to spatially vary the location of the at least one antinode with respect to the object by varying an amplitude of the microwave EM radiation generated by at least one of the plurality of EM radiation sources.

3. The system of claim 1, wherein at least one of the plurality of EM radiation sources comprises a metamaterial surface antenna.

4. The system of claim 1, wherein the controller is further configured to control the spatial variation device to spatially vary the at least one antinode according to an electroporation patter configured to regulate the generation of heat within at least the portion of the object.

5. The system of claim 1, wherein the spatial variation device comprises at least one phase changer configured to vary the phase of at least one of the EM radiation sources.

6. The system of claim 1, wherein the spatial variation device comprises a beam-director for deflecting the EM radiation.

7. The system of claim 6, wherein the beam-director comprises a meta-material beam-director.

8. The system of claim 1, wherein the spatial variation device comprises a lens to focus the EM radiation.

9. The system of claim 8, wherein the lens comprises a meta-material lens.

10. The system of claim 1, further comprising an adjustable Moire pattern generator.

11. The system of claim 1, wherein the electroporation pattern comprises a stochastic pattern.

12. The system of claim 11, wherein the controller is configured to perform multiple passes of the at least one antinode using the stochastic pattern.

13. The system of claim 12, wherein the controller is configured to allocate a rest period between successive passes of the at least one antinode.

14. The system of claim 13, further comprising varying the attribute of the electric field associated with the at least one antinode for at least one of the successive passes.

15. The system of claim 14, wherein the attribute of the electric field comprises at least one of: power, frequency characteristic, pulse length, pulse spacing, pulse duty factor, and pulse shape.

16. The system of claim 1, wherein the controller is further configured to control the exposure of the at least a portion of the object to the at least one antinode for a time period sufficient to achieve a specific amount of sterilization.

17. The system of claim 1, wherein the electroporation pattern is based on a three-dimensional model of the object.

18. The system of claim 1, wherein the at least one of the plurality of radiation sources comprises a magnetron.

19. The system of claim 1, wherein the microwave electromagnetic radiation has a wavelength between 10 cm and 0.3 cm.

* * * * *